US011468363B2

(12) United States Patent
Neumann

(10) Patent No.: US 11,468,363 B2
(45) Date of Patent: Oct. 11, 2022

(54) METHODS AND SYSTEMS FOR CLASSIFICATION TO PROGNOSTIC LABELS USING EXPERT INPUTS

(71) Applicant: Kenneth Neumann, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/502,746

(22) Filed: Jul. 3, 2019

(65) Prior Publication Data
US 2021/0004714 A1 Jan. 7, 2021

(51) Int. Cl.
*G06N 20/00* (2019.01)
*G06F 16/28* (2019.01)

(52) U.S. Cl.
CPC .......... *G06N 20/00* (2019.01); *G06F 16/285* (2019.01)

(58) Field of Classification Search
CPC .......... G06N 20/00; G06N 5/02; G06N 7/005; G06F 16/285; G16H 10/60; G16H 50/20; G16H 50/70; Y02A 90/10
See application file for complete search history.

(56) References Cited

U.S. PATENT DOCUMENTS

| 5,687,716 | A | 11/1997 | Kaufmann |
| 6,556,977 | B1 | 4/2003 | Lapointe et al. |
| 7,593,913 | B2 | 9/2009 | Wang et al. |
| 7,780,595 | B2 | 8/2010 | Iliff |
| 8,271,415 | B2 | 9/2012 | Iliff |
| 8,712,748 | B2 | 4/2014 | Thukral et al. |
| 2004/0122707 | A1 | 6/2004 | Sabol et al. |
| 2007/0100213 | A1 | 5/2007 | Kraft |

(Continued)

FOREIGN PATENT DOCUMENTS

| WO | 2001026026 | 4/2001 |
| WO | 2018039280 | 3/2018 |

OTHER PUBLICATIONS

Chen et al., "Disease Prediction by Machine Learning Over Big Data From Healthcare Communities", Apr. 26, 2017, IEEE Access, vol. 5, pp. 8869-8879 (Year: 2017).*

(Continued)

*Primary Examiner* — Brent Johnston Hoover
(74) *Attorney, Agent, or Firm* — Caldwell Intellectual Property Law

(57) ABSTRACT

A system for classification to prognostic labels using expert inputs includes a classification device. The classification device is designed and configured to record at least a physiological input pertaining to a human subject, receive at least an expert submission pertaining to the human subject, the at least an expert submission including at least a diagnostic constraint, and transmit at least a diagnostic output to a client device. The system includes a machine-learning module operating on the classification device, the machine-learning module designed and configured to receive training data relating physiological input data to diagnostic data and generate at least a diagnostic output using machine learning as a function of the training data, the at least an expert submission and the at least a physiological input.

14 Claims, 10 Drawing Sheets

(56) References Cited

U.S. PATENT DOCUMENTS

| | | | |
|---|---|---|---|
| 2009/0171871 A1* | 7/2009 | Zhang | G06N 7/005 |
| | | | 706/12 |
| 2009/0177495 A1 | 7/2009 | Abousy et al. | |
| 2014/0114677 A1 | 4/2014 | Holmes | |
| 2014/0156304 A1* | 6/2014 | Michon | G16H 50/30 |
| | | | 705/3 |
| 2017/0323064 A1 | 11/2017 | Bates | |
| 2018/0089373 A1 | 3/2018 | Matsuguchi et al. | |
| 2018/0107798 A1 | 4/2018 | Hu | |
| 2019/0019582 A1* | 1/2019 | Wallis | G16H 50/50 |
| 2019/0138693 A1 | 5/2019 | Muller et al. | |
| 2020/0258600 A1* | 8/2020 | Will | G16H 10/60 |

OTHER PUBLICATIONS

Demner-Fushman et al., "What can natural language processing do for clinical decision support?", Oct. 2009, Journal of Biomedical Informatics, vol. 42, Issue 5, pp. 760-772 (Year: 2009).*

Oguntimilehin et al., "A Machine Learning Based Clinical Decision Support System for Diagnosis and Treatment of Typhoid Fever", Jun. 2014, International Journal of Advanced Research in Computer Science and Software Engineering, vol. 4, Issue 6, pp. 961-969 (Year: 2014).*

Amato et al. Journal of Applied Biomedicine: Artificial neural networks in medical diagnosis.

* cited by examiner

METHODS AND SYSTEMS FOR CLASSIFICATION TO PROGNOSTIC LABELS USING EXPERT INPUTS

FIELD OF THE INVENTION

The present invention generally relates to the field of machine learning. In particular, the present invention is directed to methods and systems for classification to prognostic labels using expert inputs.

BACKGROUND

Automated analysis of physiological data can be highly challenging due to the multiplicity of types and sources of data to be analyzed, which in turn is a reflection of the immense complexity of systems so represented. Burgeoning knowledge concerning microscopic and macroscopic physiological states, and concomitantly expanding modes of detection and analysis of the same, have further exacerbated this problem.

SUMMARY OF THE DISCLOSURE

In one aspect, a system for classification to prognostic labels using expert inputs includes a classification device. The classification device is designed and configured to record at least a physiological input pertaining to a human subject, receive at least an expert submission pertaining to the human subject, the at least an expert submission including at least a diagnostic constraint, and transmit at least a diagnostic output to a client device. The system includes a machine-learning module operating on the classification device, the machine-learning module designed and configured to receive training data relating physiological input data to diagnostic data and generate at least a diagnostic output using machine learning as a function of the training data, the at least an expert submission and the at least a physiological input.

In another aspect, a method of classification to prognostic labels using expert inputs includes recording, at a classification device, at least a physiological input pertaining to a human subject. The method includes receiving, at the classification device, at least an expert submission pertaining to the human subject, the at least an expert submission including at least a diagnostic constraint. The method includes receiving, at the classification device, training data relating physiological input data to diagnostic data. The method includes generating, by the classification device, at least a diagnostic output using machine learning as a function of the at least an expert submission and the at least a physiological input. The method includes transmitting, by the classification device, at least a diagnostic output to a client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments of systems and methods disclosed herein may classify physiological samples to one or more prognostic labels using training sets correlating physiological state data to prognostic labels; prognostic labels are further linked to ameliorative process labels 144 using additional training sets. Categorization of data elements in training sets may be accomplished using unsupervised clustering algorithms; categorization may alternatively or additionally involve expert data inputs provided by graphical user interface 108 entries or extracted using language processing algorithms from a corpus of subject-specific documents. Expert submissions are used to focus the generative process, which may be accomplished by pruning training data 120, selection of particular machine-learning models, filtering output, or the like.

Figure 1:
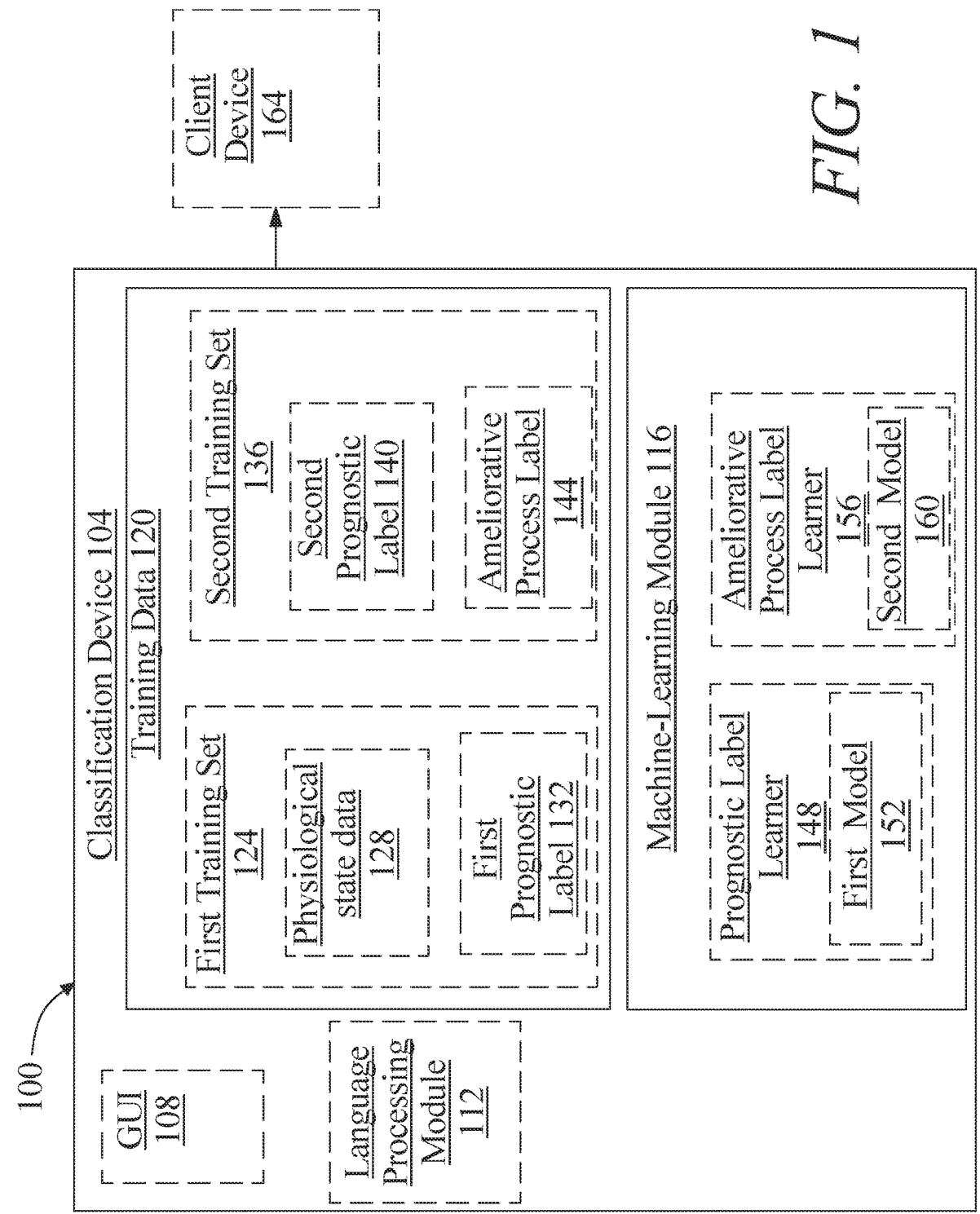
FIG. 1 is a block diagram illustrating an exemplary embodiment of a system for classification to prognostic labels using expert inputs.

Referring now to the FIG. 1, an exemplary embodiment of a system 100 classification to prognostic labels using expert inputs. System 100 includes a classification device 104. Classification device 104 may include any computing device as described below in reference to FIG. 10, including without limitation a microcontroller, microprocessor, digital signal processor (DSP) and/or system on a chip (SoC) as described below in reference to FIG. 10. Classification device 104 may be housed with, may be incorporated in, or may incorporate one or more sensors of at least a sensor. Computing device may include, be included in, and/or communicate with a mobile device such as a mobile telephone or smartphone. Classification device 104 may include a single computing device operating independently, or may include two or more computing device operating in concert, in parallel, sequentially or the like; two or more computing devices may be included together in a single computing device or in two or more computing devices. Classification device 104 with one or more additional devices as described below in further detail via a network interface device. Network interface device may be utilized for connecting a classification device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Classification device 104 may include but is not limited to, for example, a classification device 104 or cluster of computing devices in a first location and a second computing device or cluster of computing devices in a second location. Classification device 104 may include one or more computing devices dedicated to data storage, security, distribution of traffic for load balancing, and the like. Classification device 104 may distribute one or more computing tasks as described below across a plurality of computing devices of computing device, which may operate in parallel, in series, redundantly, or in any other manner used for distribution of tasks or memory between computing devices. Classification device 104 may be implemented using a "shared nothing" architecture in which data is cached at the worker, in an embodiment, this may enable scalability of system 100 and/or computing device.

Still referring to FIG. 1, classification device 104 and/or one or more modules operating thereon may be designed and/or configured to perform any method, method step, or sequence of method steps in any embodiment described in this disclosure, in any order and with any degree of repetition. For instance, classification device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Classification device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. Any module or modules introduced in this disclosure may be instantiated using any combination of software and/or hardware commands or circuitry as described in this disclosure, including without limitation logic circuits, software programs using functions, methods, and/or object-oriented programming, or the like. Although modules are introduced conceptually in the ensuing disclosure as separate components for the sake of clarity, persons skilled in the art, upon reviewing the entirety of this disclosure, will be aware that a module may be created, as contemplated in the scope of this disclosure, by any combination of circuitry and/or software program commands stored in any form; for instance, and without limitation, a module may not be identified within system 100 and/or classification device 104 as a distinct entity or component, but may exist only as the combination of elements and/or commands performing the functions attributed herein to the module, and two or more modules may be partially or wholly combined together, may share functions, data, objects, and/or circuits.

With continued reference to FIG. 1, classification device 104 is designed and configured to record at least a physiological input pertaining to a human subject. A "physiological input" as used in this disclosure, is an element of data describing information relevant to human subject's constitutional state, including without limitation symptoms, conditions, prognoses, test results, concerns, reasons for a visit to a health professional, personal stories and/or information concerning the human subject's interests, relationships to other people, informal and/or formal personal or health support groups or persons, or the like. At least a physiological input may include, without limitation, at least a biological extraction. At least a biological extraction, as used herein, includes may include any element and/or elements of data suitable for use as an element of physiological state data 128. Physiological state data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibronigen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules 112 as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

At least a biological extraction may include a physically extracted sample, where a "physically extracted sample" as used in this disclosure is a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of system 100 or may be a separate device in communication with system 100.

Still referring to FIG. 1, at least a first biological extraction may include data describing one or more test results, including results of mobility tests, stress tests, dexterity tests, endocrinal tests, genetic tests, psychological tests and/or evaluations, electromyographic tests, biopsies, radiological tests, genetic tests, and/or sensory tests. Persons skilled in the art, upon reviewing the entirety of this disclosure, will be aware of various additional examples of at least a physiological sample consistent with this disclosure. At least a physiological sample may be added to a database, such as a physiological sample database as described in further detail below.

With continued reference to FIG. 1, at least a physiological input may include at least a prognostic label. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a prognostic label may be associated with a physical and/or somatic condition, a mental condition such as a mental illness, neurosis, or the like, or any other condition affecting human health that may be associated with one or more elements of physiological state data as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

Continuing to refer to FIG. 1, at least a physiological input may include at least an ameliorative process label 144. As used herein, an ameliorative process label 144 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Still referring to FIG. 1, at least a physiological input may include without limitation a reason for a human subject's current visit with a health professional. At least a physiological input may include current status of following treatment plan with identified areas of focus. At least a physiological input may include personal story about a user such as who they are, what they care about, and who supports them.

Continuing to refer to FIG. 1, classification device 104 is designed and configured to receive at least an expert submission pertaining to the human subject. At least an expert submission, as used herein, is a submission provided by an expert in subjects pertaining to constitutional state of human subject, including without limitation expertise in a physiological state and/or status of human subject, in any test result and/or physiological state data as described above, in any subject described by a prognostic label as described above, in any subject that may be described using an ameliorative process label 144 as described above, or the like. At least an expert submission may be received, as a non-limiting example, from a medical professional such as a doctor, nurse, therapist, psychologist, medical technician, or the like. At least an expert submission may be received via and/or from a client device operated by an expert, such as a computer and/or computer system operated in a medical professional's office, such as a doctor's office, a computing device incorporated in one or more medical devices, a mobile device operated by the expert, or the like.

Still referring to FIG. 1, at least an expert submission includes at least a diagnostic constraint. As used in this disclosure, a "diagnostic constraint" is an element of data restricting data, concerning a human subject, to be used in or produced by a machine-learning module 116 as described in further detail below to a smaller subset than the total set of all data concerning the human subject that could be used or produced by machine-learning module 116 as described in further detail below; restriction may include generating and/or selecting a smaller subset of biological extraction data concerning the human subject, generating and/or selecting a smaller subset of training data 120, as described in further detail below, to be used by machine-learning module 116, generating and/or selecting a smaller subset of machine-learning models, as described in further detail below, to be used by machine-learning module 116, generating and/or selecting a smaller subset of machine-learning processes, as described in further detail below, to be used by machine-learning module 116, generating and/or selecting a smaller subset of learners incorporated in machine-learning module 116, as described in further detail below, to be used by machine-learning module 116, and/or generating, filtering to, and/or selecting a smaller subset of machine-learning outputs, as described in further detail below, to be produced by machine-learning module 116. Diagnostic constraint may include, for instance, a selection of what information a doctor or other expert needs system to generate such as diagnostic output, treatment plans, or the like. Diagnostic constraint may include a symptom, test result, particular biological extraction, and/or evaluation from a physical examination with human subject, a phone call with human subject, or the like. Persons skilled in the art, upon reviewing the entirety of this disclosure, will be aware of various additional examples of diagnostic constraints as defined herein.

With continued reference to FIG. 1, classification device 104 may receive the at least an expert submission according to any suitable process. In an embodiment, classification device 104 and/or a user device connected to classification device 104 may provide a graphical user interface 108, which may include without limitation a form or other graphical element having data entry fields, wherein an experts, may enter at least a diagnostic constraint; fields in graphical user interface 108 may provide options describing previously identified diagnostic constraints, which may include a comprehensive or near-comprehensive list commonly selected, and/or previously entered diagnostic constraints, for instance in "drop-down" lists, where an expert may be able to select one or more entries to indicate selections of diagnostic constraints. Fields may include free-form entry fields such as text-entry fields where an expert may be able to type or otherwise enter text, enabling expert to describe a diagnostic constraint not listed in a drop-down list or the like. Graphical user interface 108 or the like may include fields corresponding to prognostic labels, ameliorative process labels 144, elements of physiological state data, and/or biological extractions concerning, associated with, or extracted from human subject; for instance, an expert may be able to select one or more such data elements of interest so as to identify data to which diagnostic constraint will constrain input and/or output data, and/or to identify data that expert wishes to eliminate from input and/or output using at least a diagnostic constraint.

Still referring to FIG. 1, at least an expert submission may a textual submission such as without limitation text entered by an expert in a textual entry field, received from expert via electronic communication, or the like. Classification device 104 may include a language processing module 112 designed and configured to parse the at least a textual submission and extract the at least a diagnostic constraint. Language processing module 112 may include any hardware and/or software module. Language processing module 112 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 112 may compare extracted words to diagnostic constraints and/or subjects of diagnostic constraints such as without limitation, data, categories of data including categories of data as set forth in further detail below, categories of training data 120 such as without limitation data identifying cohorts including human subject, machine-learning models such as without limitation machine-learning modules 116 relating to cohorts including human subject, prognostic labels of interest to the expert, ameliorative labels of interest to the expert, biological extraction data of interest to the expert, and/or physiological stat data of interest to the expert, learners, categories of outputs, of the like. In an embodiment, one or more diagnostic constraints and/or subjects of diagnostic constraints may be enumerated, to find total count of mentions in textual data. Alternatively or additionally, language processing module 112 may operate to produce a language processing model. Language processing model may include a program automatically generated by classification device 104 and/or language processing module 112 to produce associations between one or more words extracted from at least a document and detect associations, including without limitation mathematical associations, between such words, and/or associations of extracted words with diagnostic constraints and/or subjects of diagnostic constraints. Associations between language elements, where language elements include for purposes herein extracted words, diagnostic constraints and/or subjects of diagnostic constraints may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given diagnostic constraint and/or subject of diagnostic constraints. As a further example, statistical correlations and/or mathematical associations may include probabilistic formulas or relationships indicating a positive and/or negative association between at least an extracted word and/or a diagnostic constraint and/or subject of diagnostic constraints; positive or negative indication may include an indication that a given document is or is not indicating a diagnostic constraint and/or subjects of diagnostic constraint is or is not associated with a given word. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at classification device 104, or the like.

Still referring to FIG. 1, language processing module 112 and/or classification device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 112 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 112 may use a corpus of documents to generate associations between language elements in a language processing module 112, and classification device 104 may then use such associations to analyze words extracted from one or more documents and determine that the one or more documents indicate significance of an association between at least an extracted word and/or a diagnostic constraint and/or subject of diagnostic constraints. In an embodiment, classification device 104 may perform this analysis using a selected set of significant documents, such as documents identified by one or more experts as representing good science, good clinical analysis, or the like; an expert or experts may identify or enter such documents via graphical user interface 108 as described in further detail below, or may communicate identities of significant documents according to any other suitable method of electronic communication, or by providing such identity to other persons who may enter such identifications into classification device 104. Documents may be entered into classification device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device 104 may automatically obtain the document using such an identifier, for instance by submitting a request to a database or compendium of documents such as JSTOR as provided by Ithaka Harbors, Inc. of New York.

Continuing to refer to FIG. 1, system 100 may include a machine-learning module 116 operating on the classification device 104. Machine-learning module 116 may include any suitable hardware or software module as described herein or any combination thereof. Machine-learning module 116 is designed and configured to receive training data 120. Training data 120, as used herein, is data containing correlation that a machine-learning process may use to model relationships between two or more categories of data elements. For instance, and without limitation, training data 120 may include a plurality of data entries, each entry representing a set of data elements that were recorded, received, and/or generated together; data elements may be correlated by shared existence in a given data entry, by proximity in a given data entry, or the like. Multiple data entries in training data 120 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 120 according to various correlations; correlations may indicate causative and/or predictive links between categories of data elements, which may be modeled as relationships such as mathematical relationships by machine-learning processes as described in further detail below. Training data 120 may be formatted and/or organized by categories of data elements, for instance by associating data elements with one or more descriptors corresponding to categories of data elements. As a non-limiting example, training data 120 may include data entered in standardized forms by persons or processes, such that entry of a given data element in a given field in a form may be mapped to one or more descriptors of categories. Elements in training data 120 may be linked to descriptors of categories by tags, tokens, or other data elements; for instance, and without limitation, training data 120 may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data 120 may include one or more elements that are not categorized; that is, training data 120 may not be formatted or contain descriptors for some elements of data. Machine-learning algorithms and/or other processes may sort training data 120 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 120 to be made applicable for two or more distinct machine-learning algorithms as described in further detail below.

With continued reference to FIG. 1, machine-learning module 116 is designed and configured to receive training data 120 relating physiological input data to diagnostic data. "Diagnostic data," as used herein, is data describing prognostic and/or ameliorative data relating to a human subject; diagnostic data may include, without limitation, data usable for and/or labeled by prognostic labels and/or data usable for and/or labeled by ameliorative process labels 144. Training data 120 relating physiological input data to diagnostic data may include a plurality of entries, each entry including at least an element of physiological input data and at least a correlated element of diagnostic data; for instance, and without limitation, an entry may include an element of physiological state data 128 and a prognostic label, an element of physiological state data 128 and an ameliorative process label 144, a prognostic label and an ameliorative process label 144, and/or a combination of an element of physiological state data 128, a prognostic label, and an ameliorative process label 144.

As a non-limiting, illustrative example, and still referring to FIG. 1, categorization device 104 may be configured to receive a first training set 124 including a plurality of first data entries, each first data entry of the first training set 124 including at least an element of physiological state data 128 and at least a correlated first prognostic label 132. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the first training set 124. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 124 and/or first data element consistently with this disclosure.

In an embodiment, and still referring to FIG. 1, classification device 104 may be designed and configured to associate at least an element of physiological state data 128 with at least a category from a list of significant categories of physiological state data. Significant categories of physiological state data may include labels and/or descriptors describing types of physiological state data that are identified as being of high relevance in identifying prognostic labels. As a non-limiting example, one or more categories may identify significant categories of physiological state data based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, classification device 104 may receive the list of significant categories according to any suitable process; for instance, and without limitation, classification device 104 may receive the list of significant categories from at least an expert. In an embodiment, classification device 104 and/or a user device connected to classification device 104 may provide a graphical user interface 108 as described above, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface 108 may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 108 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface 108 may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with expert entries, or the like.

Referring again to FIG. 1, data information describing significant categories of physiological data, relationships of such categories to prognostic labels, and/or significant categories of prognostic labels may alternatively or additionally be extracted from one or more documents using a language processing module 112 as described above.

Still referring to FIG. 1, language processing module 112 may compare extracted words to categories of physiological data recorded at classification device 104, one or more prognostic labels recorded at classification device 104, and/or one or more categories of prognostic labels recorded at classification device 104; such data for comparison may be entered on classification device 104 as described above using expert data inputs or the like. In an embodiment, one or more categories may be enumerated, to find total count of mentions in such documents. Alternatively or additionally, language processing module 112 may operate to produce a language processing model. Language processing model may include a program automatically generated by classification device 104 and/or language processing module 112 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at classification device 104, or the like.

Still referring to FIG. 1, language processing module 112 may use a corpus of documents, for instance as described above, to generate associations between language elements in a language processing module 112, and classification device 104 may then use such associations to analyze words extracted from one or more documents and determine that the one or more documents indicate significance of a category of physiological data, a given relationship of such categories to prognostic labels, and/or a given category of prognostic labels. In an embodiment, classification device 104 may perform this analysis using a selected set of significant documents, such as documents identified by one or more experts as representing good science, good clinical analysis, or the like; experts may identify or enter such documents via graphical user interface 108 as described above in reference to FIG. 9, or may communicate identities of significant documents according to any other suitable method of electronic communication, or by providing such identity to other persons who may enter such identifications into classification device 104. Documents may be entered into classification device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface 108, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, classification device 104 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, classification device 104 may be configured, for instance as part of receiving the first training set 124, to associate at least correlated first prognostic label 132 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result classification device 104 may modify list of significant categories to reflect this difference.

Still referring to FIG. 1, classification device 104 is designed and configured to receive a second training set 136 including a plurality of second data entries. Each second data entry of the second training set 136 includes at least a second prognostic label 140; at least a second prognostic label 140 may include any label suitable for use as at least a first prognostic label 132 as described above. Each second data entry of the second training set 136 includes at least an ameliorative process label 144, as described above, correlated with the at least a second prognostic label 140, where correlation may include any correlation suitable for correlation of at least a first prognostic label 132 to at least an element of physiological data as described above.

Continuing to refer to FIG. 1, in an embodiment classification device 104 may be configured, for instance as part of receiving second training set 136, to associate the at least second prognostic label 140 with at least a category from a list of significant categories of prognostic labels. This may be performed as described above for use of lists of significant categories with regard to at least a first prognostic label 132. Significance may be determined, and/or association with at least a category, may be performed for prognostic labels in first training set 124 according to a first process as described above and for prognostic labels in second training set 136 according to a second process as described above.

Still referring to FIG. 1, classification device 104 may be configured, for instance as part of receiving second training set 136, to associate at least a correlated ameliorative process label 144 with at least a category from a list of significant categories of ameliorative process labels 144. In an embodiment, classification device 104 and/or a user device connected to classification device 104 may provide a second graphical user interface 108 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface 108 may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 108 or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface 108 may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 112 or the like as described above.

In an embodiment, and still referring to FIG. 1, classification device 104 may extract at least a second data entry from one or more documents; extraction may be performed using any language processing method as described above. Classification device 104 may be configured, for instance as part of receiving second training set 136, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 144; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 144, and/or efficacy of ameliorative process labels 144 may be extracted from and/or determined from one or more medical history documents using any processes for language processing as described above; for instance, language processing module 112 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 1, classification device 104 may be configured, for instance as part of receiving second training set 136, to receiving at least a second data entry of the plurality of second data entries from at least an expert. This may be performed, without limitation using second graphical user interface 108 as described above. Additional training sets may be received as part of training data 120; for instance, a third training set (not shown) may be received including a plurality of third data entries, each data entry of the plurality of third data entries including at least a physiological state data element and at least a correlated second ameliorative process label 144. Any data entry of any of first, second, or third training sets may include additional correlated data; thus one or more data entries of first data set may include correlated ameliorative process labels 144, one or more data entries of second data set may include correlated physiological state data elements, and/or one or more data entries of third data set may include correlated prognostic labels.

Figure 2:
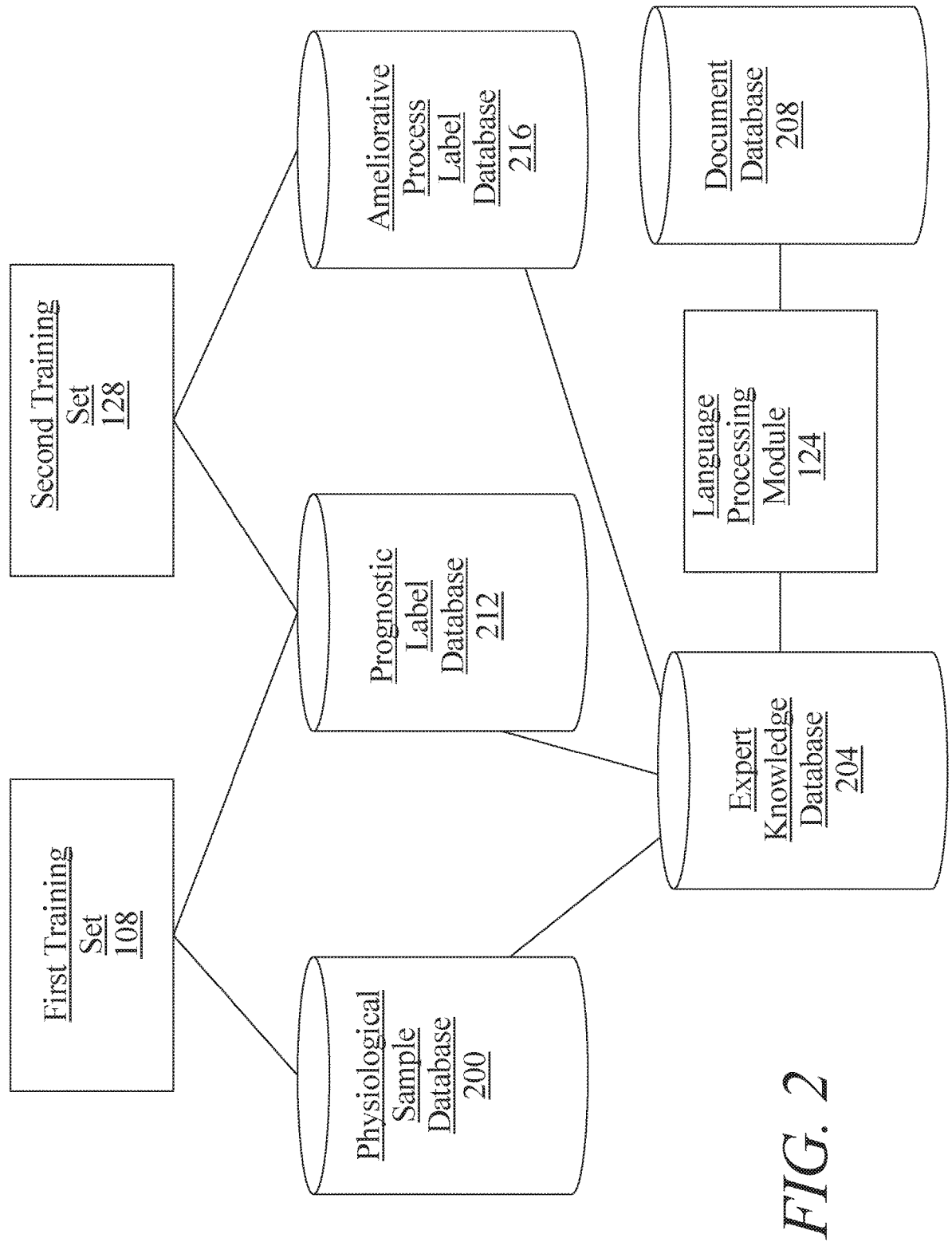
FIG. 2 is a block diagram illustrating embodiments of data storage facilities for use in disclosed systems and methods.

Referring now to FIG. 2, data incorporated in at least a physiological input, at least an expert submission, and/or in training data 120, including without limitation in first training set 124, second training set 136, and/or third training set, may be incorporated in one or more databases. As a non-limiting example, one or elements of physiological state data may be stored in and/or retrieved from a physiological sample database 200. A physiological sample database 200 may include any data structure for ordered storage and retrieval of data, which may be implemented as a hardware or software module. A physiological sample database 200 may be implemented, without limitation, as a relational database, a key-value retrieval datastore such as a NOSQL database, or any other format or structure for use as a datastore that a person skilled in the art would recognize as suitable upon review of the entirety of this disclosure. A physiological sample database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a physiological sample database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a physiological sample database 200 may reflect categories, cohorts, and/or populations of data consistently with this disclosure.

Figure 3:
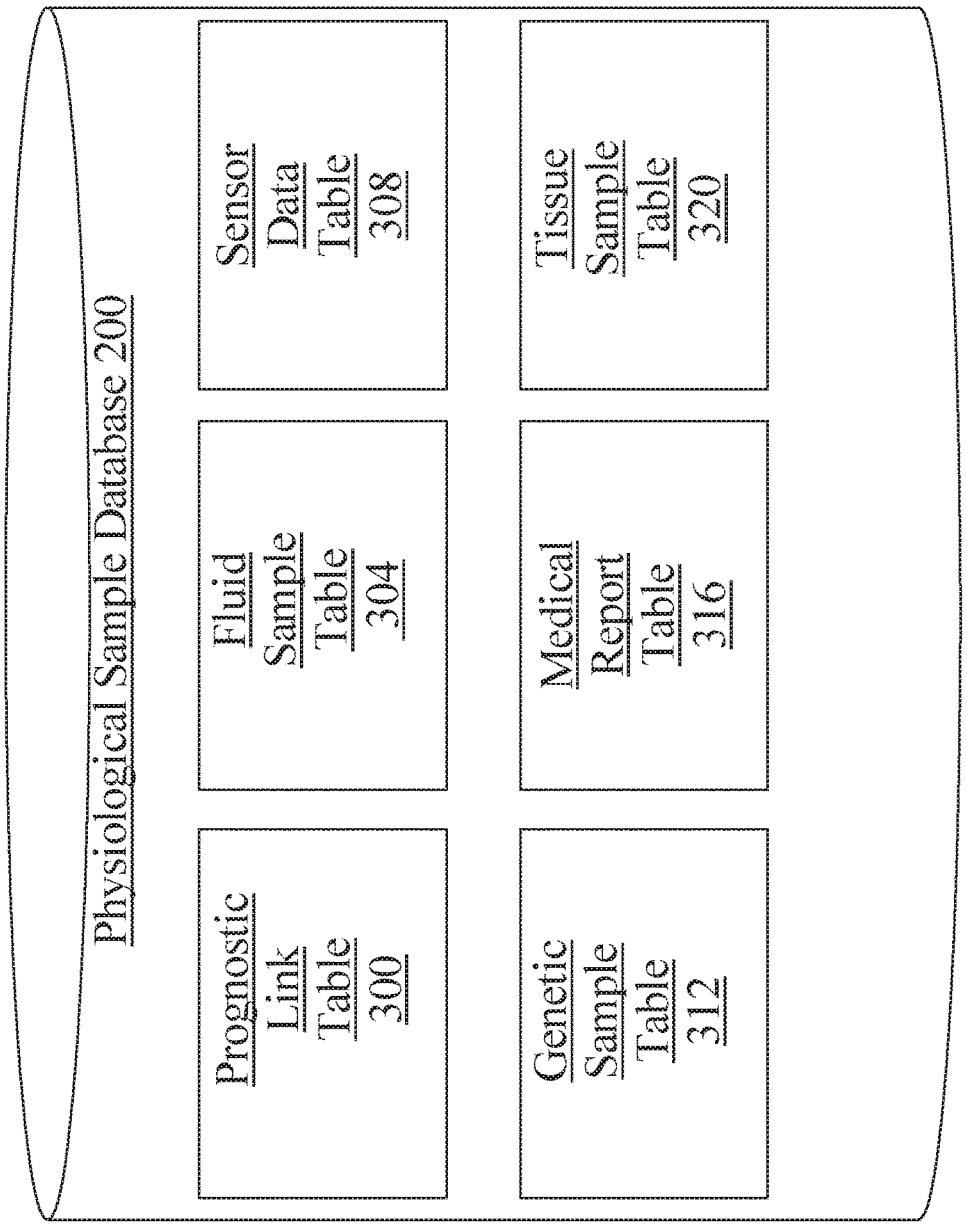
FIG. 3 is a block diagram illustrating an exemplary embodiment of a physiological sample database.

Referring now to FIG. 3, one or more database tables in physiological sample database 200 may include, as a non-limiting example, a prognostic link table 300. Prognostic link table 300 may be a table relating physiological sample data as described above to prognostic labels; for instance, where an expert has entered data relating a prognostic label to a category of physiological sample data and/or to an element of physiological sample data via graphical user interface 108 as described above, one or more rows recording such an entry may be inserted in prognostic link table 300. Alternatively or additionally, linking of prognostic labels to physiological sample data may be performed entirely in a prognostic label database as described below.

With continued reference to FIG. 3, physiological sample database 200 may include tables listing one or more samples according to sample source. For instance, and without limitation, physiological sample database 200 may include a fluid sample table 304 listing samples acquired from a person by extraction of fluids, such as without limitation blood, lymph cerebrospinal fluid, or the like. As another non-limiting example, physiological sample database 200 may include a sensor data table 308, which may list samples acquired using one or more sensors, for instance as described in further detail below. As a further non-limiting example, physiological sample database 200 may include a genetic sample table 312, which may list partial or entire sequences of genetic material. Genetic material may be extracted and amplified, as a non-limiting example, using polymerase chain reactions (PCR) or the like. As a further example, also non-limiting, physiological sample database 200 may include a medical report table 316, which may list textual descriptions of medical tests, including without limitation radiological tests or tests of strength and/or dexterity or the like. Data in medical report table may be sorted and/or categorized using a language processing module 112 312, for instance, translating a textual description into a numerical value and a label corresponding to a category of physiological data; this may be performed using any language processing algorithm or algorithms as referred to in this disclosure. As another non-limiting example, physiological sample database 200 may include a tissue sample table 320, which may record physiological samples obtained using tissue samples. Tables presented above are presented for exemplary purposes only; persons skilled in the art will be aware of various ways in which data may be organized in physiological sample database 200 consistently with this disclosure.

Referring again to FIG. 2, classification device 104 and/or another device in system 100 may populate one or more fields in physiological sample database 200 using expert information, which may be extracted or retrieved from an expert knowledge database 204. An expert knowledge database 204 may include any data structure and/or data store suitable for use as a physiological sample database 200 as described above. Expert knowledge database 204 may include data entries reflecting one or more expert submissions of data such as may have been submitted according to any process described above in reference to FIG. 1, including without limitation by using graphical user interface 108 and/or second graphical user interface 108. Expert knowledge database may include one or more fields generated by language processing module 112, such as without limitation fields extracted from one or more documents as described above. For instance, and without limitation, one or more categories of physiological data and/or related prognostic labels and/or categories of prognostic labels associated with an element of physiological state data 128 as described above may be stored in generalized from in an expert knowledge database 204 and linked to, entered in, or associated with entries in a physiological sample database 200. Documents may be stored and/or retrieved by classification device 104 and/or language processing module 112 in and/or from a document database 208; document database 208 may include any data structure and/or data store suitable for use as physiological sample database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
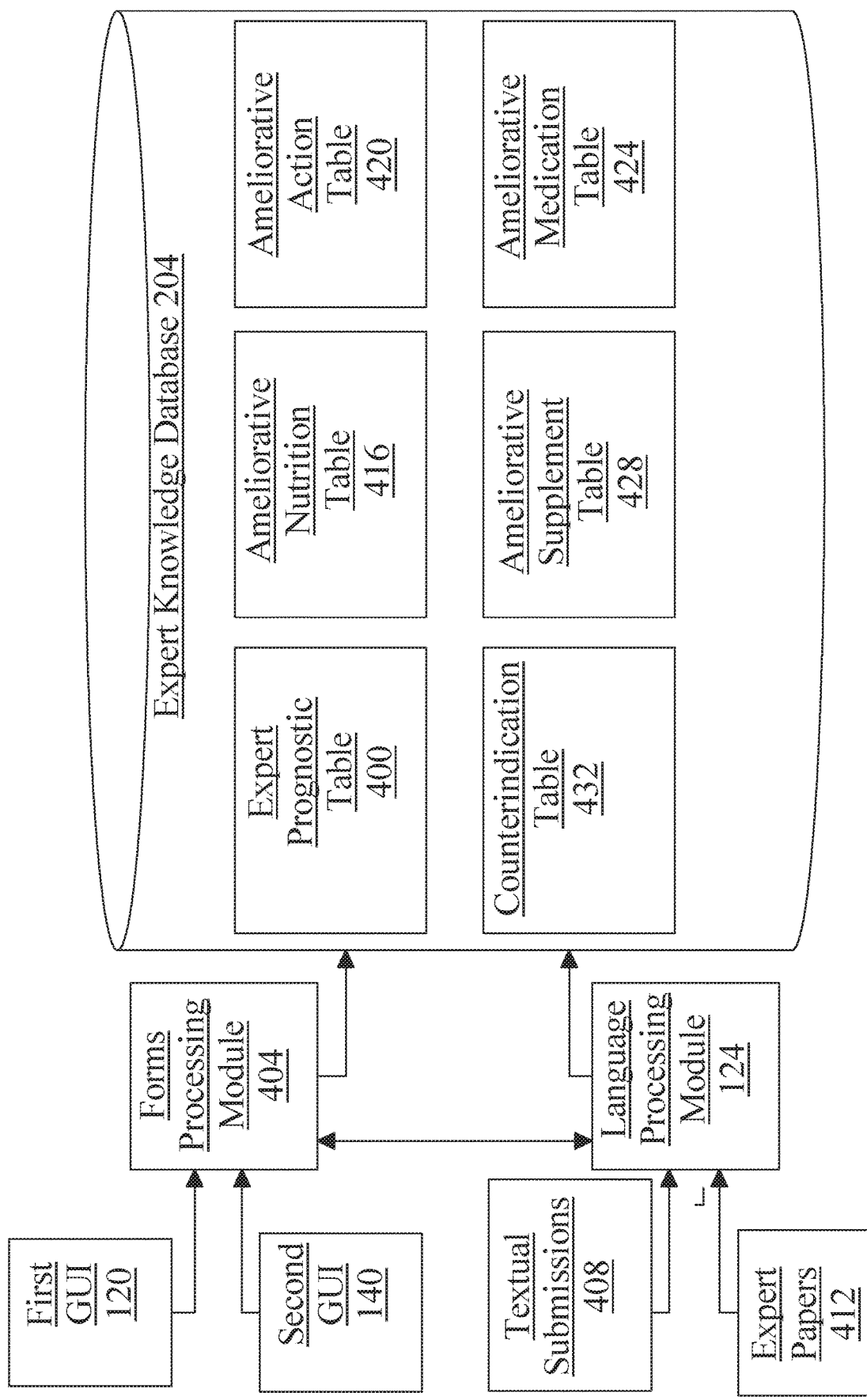
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via graphical user interface 108 as described above, one or more rows recording such an entry may be inserted in expert prognostic table 400. In an embodiment, a forms processing module 404 may sort data entered in a submission via graphical user interface 108 by, for instance, sorting data from entries in the graphical user interface 108 to related categories of data; for instance, data entered in an entry relating in the graphical user interface 108 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 112 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 112 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 112. Data may be extracted from expert papers 412, which may include without limitation publications in medical and/or scientific journals, by language processing module 112 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a further non-limiting example tables listing one or more ameliorative process labels 144; expert data populating such tables may be provided, without limitation, using any process described above, including entry of data from second graphical user interface 108 via forms processing module 404 and/or language processing module 112, processing of textual submissions 408, or processing of expert papers 412. For instance, and without limitation, an ameliorative nutrition table 416 may list one or more ameliorative processes based on nutritional instructions, and/or links of such one or more ameliorative processes to prognostic labels, as provided by experts according to any method of processing and/or entering expert data as described above. As a further example an ameliorative action table 420 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above. As an additional example, an ameliorative supplement table 424 may list one or more ameliorative processes based on nutritional supplements, such as vitamin pills or the like, and/or links of such one or more ameliorative processes to prognostic labels, as provided by experts according to any method of processing and/or entering expert data as described above. As a further non-limiting example, an ameliorative medication table 428 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above. As an additional example, a counterindication table 432 may list one or more counterindications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like. Tables presented above are presented for exemplary purposes only; persons skilled in the art will be aware of various ways in which data may be organized in expert knowledge database 204 consistently with this disclosure.

Referring again to FIG. 2, a prognostic label database 212, which may be implemented in any manner suitable for implementation of physiological sample database 200, may be used to store prognostic labels used in system 100, including any prognostic labels correlated with elements of physiological data in first training set 124 as described above; prognostic labels may be linked to or refer to entries in physiological sample database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in physiological sample database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

Figure 5:
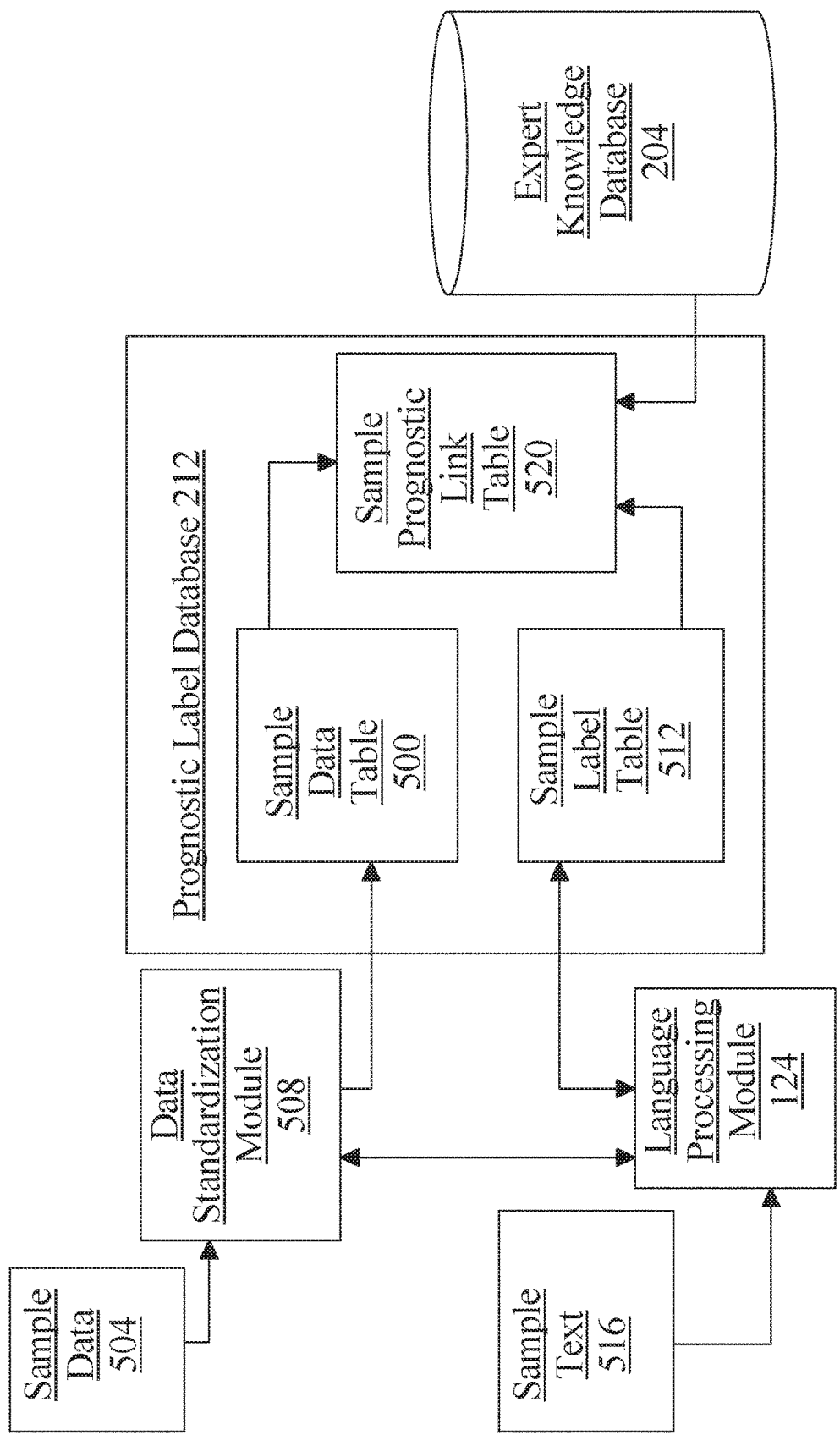
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from physiological sample database 200, in a raw or unsorted form, and may be translated into standard forms, such as standard units of measurement, labels associated with particular physiological data values, or the like; this may be accomplished using a data standardization module 508, which may perform unit conversions or the like. Data standardization module 508 may alternatively or additionally map textual information, such as labels describing values tested for or the like, using language processing module 112 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 112 may compare textual information so received to prognostic labels and/or form new prognostic labels according to any suitable process as described above. A sample prognostic link table 520 may combine samples with prognostic labels, as acquired from sample label table 512 and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Referring again to FIG. 2, first training set 124 may be populated by retrieval of one or more records from physiological sample database 200 and/or prognostic label database 212; in an embodiment, entries retrieved from physiological sample database 200 and/or prognostic label database 212 may be filtered and or select via query to match one or more additional elements of information as described above, so as to retrieve a first training set 124 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from physiological sample database 200 and/or prognostic label database to generate a first training set 124 to reflect individualized group data pertaining to a person of interest in operation of system and/or method, including without limitation a person with regard to whom at least a physiological sample is being evaluated as described in further detail below. Classification device 104 may alternatively or additionally receive a first training set 124 and store one or more entries in physiological sample database 200 and/or prognostic label database 212 as extracted from elements of first training set 124.

Still referring to FIG. 2, system 100 may include or communicate with an ameliorative process label 144 database 216; an ameliorative process label 144 database 216 may include any data structure and/or datastore suitable for use as a physiological sample database 200 as described above. An ameliorative process label 144 database 216 may include one or more entries listing labels associated with one or more ameliorative processes as described above, including any ameliorative labels correlated with prognostic labels in second training set 136 as described above; ameliorative process labels 144 may be linked to or refer to entries in prognostic label database 212 to which ameliorative process labels 144 correspond. Linking may be performed by reference to historical data concerning prognostic labels, such as therapies, treatments, and/or lifestyle or dietary choices chosen to alleviate conditions associated with prognostic labels in the past; alternatively or additionally, a relationship between an ameliorative process label 144 and a data entry in prognostic label database 212 may be determined by reference to a record in an expert knowledge database 204 linking a given ameliorative process label 144 to a given category of prognostic label as described above. Entries in ameliorative process label 144 database 212 may be associated with one or more categories of prognostic labels as described above, for instance using data stored in and/or extracted from an expert knowledge database 204.

Figure 6:
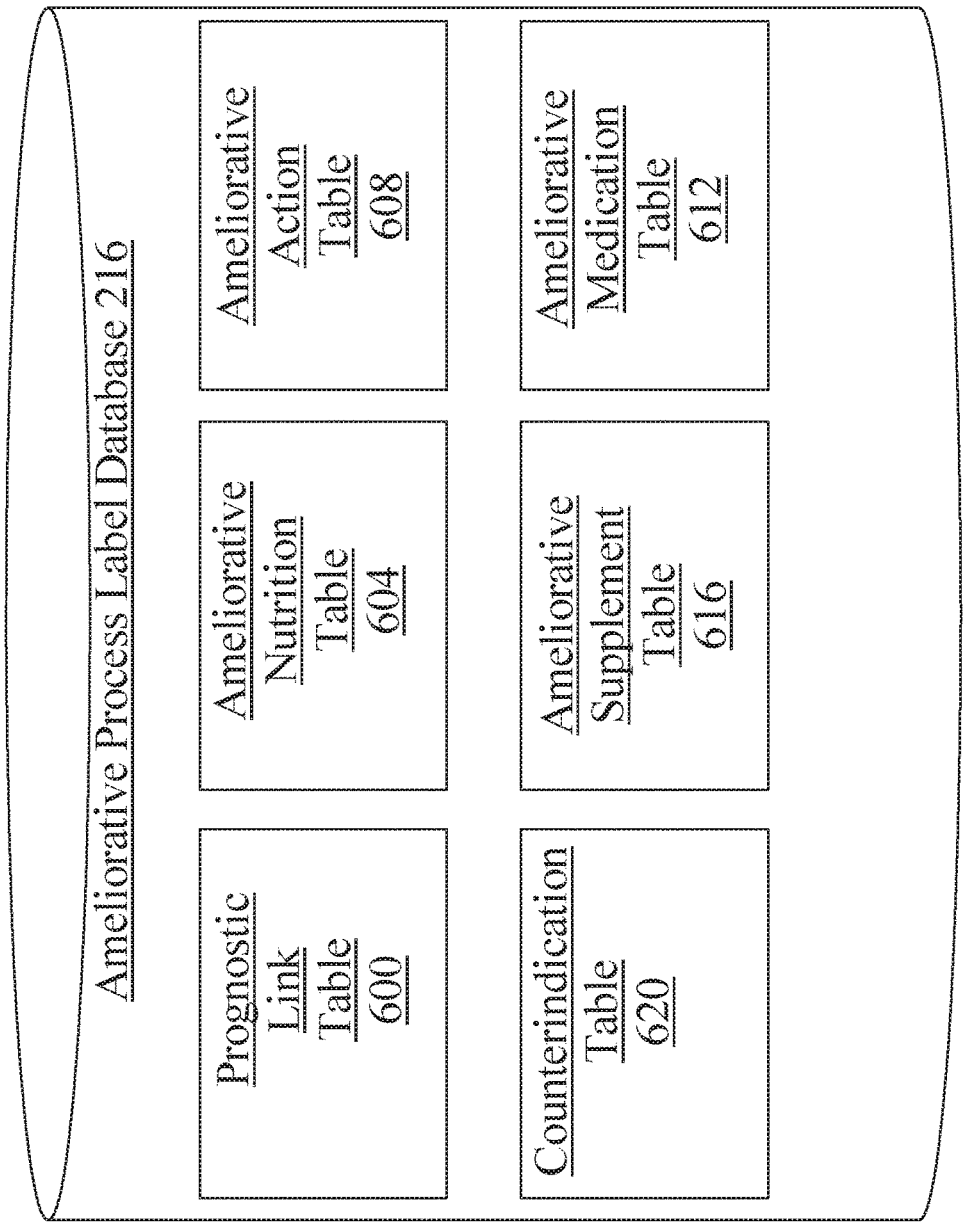
FIG. 6 is a block diagram illustrating an exemplary embodiment of an ameliorative process label 144 database.

Referring now to FIG. 6, an exemplary embodiment of an ameliorative process label 144 database 216 is illustrated. Ameliorative process label 144 database 216 may, as a non-limiting example, organize data stored in the ameliorative process label 144 database 216 according to one or more database tables. One or more database tables may be linked to one another by, for instance, common column values. For instance, a common column between two tables of ameliorative process label 144 database 216 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, ameliorative process label 144 database 216 may include a prognostic link table 600; prognostic link table may link ameliorative process data to prognostic label data, using any suitable method for linking data in two or more tables as described above. Ameliorative process label 144 database 216 may include an ameliorative nutrition table 604, which may list one or more ameliorative processes based on nutritional instructions, and/or links of such one or more ameliorative processes to prognostic labels, for instance as provided by experts according to any method of processing and/or entering expert data as described above, and/or using one or more machine-learning processes as set forth in further detail below. As a further example an ameliorative action table 608 may list one or more ameliorative processes based on instructions for actions a user should take, including without limitation exercise, meditation, and/or cessation of harmful eating, substance abuse, or other habits, and/or links of such one or more ameliorative processes to prognostic labels, as provided by experts according to any method of processing and/or entering expert data as described above and/or using one or more machine-learning processes as set forth in further detail below. As an additional example, an ameliorative supplement table 612 may list one or more ameliorative processes based on nutritional supplements, such as vitamin pills or the like, and/or links of such one or more ameliorative processes to prognostic labels, as provided by experts according to any method of processing and/or entering expert data as described above and/or using one or more machine-learning processes as set forth in further detail below. As a further non-limiting example, an ameliorative medication table 616 may list one or more ameliorative processes based on medications, including without limitation over-the-counter and prescription pharmaceutical drugs, and/or links of such one or more ameliorative processes to prognostic labels, as provided by experts according to any method of processing and/or entering expert data as described above and/or using one or more machine-learning processes as set forth in further detail below. As an additional example, a counterindication table 620 may list one or more counter-indications for one or more ameliorative processes; counterindications may include, without limitation allergies to one or more foods, medications, and/or supplements, side-effects of one or more medications and/or supplements, interactions between medications, foods, and/or supplements, exercises that should not be used given one or more medical conditions, injuries, disabilities, and/or demographic categories, or the like; this may be acquired using expert submission as described above and/or using one or more machine-learning processes as set forth in further detail below. Tables presented above are presented for exemplary purposes only; persons skilled in the art will be aware of various ways in which data may be organized in ameliorative process database 216 consistently with this disclosure.

Referring again to FIG. 2, second training set 136 may be populated by retrieval of one or more records from prognostic label database 212 and/or ameliorative process label 144 database 216; in an embodiment, entries retrieved from prognostic label database 212 and/or ameliorative process label 144 database 216 may be filtered and or select via query to match one or more additional elements of information as described above, so as to retrieve a second training set 136 including data belonging to a given cohort, demographic population, or other set, so as to generate outputs as described below that are tailored to a person or persons with regard to whom system 100 classifies prognostic labels to ameliorative process labels 144 as set forth in further detail below. Persons skilled in the art, upon reviewing the entirety of this disclosure, will be aware of various ways in which records may be retrieved from prognostic label database 212 and/or ameliorative process label 144 database 216 to generate a second training set 136 to reflect individualized group data pertaining to a person of interest in operation of system and/or method, including without limitation a person with regard to whom at least a physiological sample is being evaluated as described in further detail below. Classification device 104 may alternatively or additionally receive a second training set 136 and store one or more entries in prognostic label database 212 and/or ameliorative process label 144 database 216 as extracted from elements of second training set 136.

In an embodiment, and still referring to FIG. 2, classification device 104 may receive an update to one or more elements of data represented in first training set 124 and/or second training set 136, and may perform one or more modifications to first training set 124 and/or second training set 136, or to physiological sample database 200, expert knowledge database 204, prognostic label database 212, and/or ameliorative process label 144 database 216 as a result. For instance a physiological sample may turn out to have been erroneously recorded; classification device 104 may remove it from first training set 124, second training set 136, physiological sample database 200, expert knowledge database 204, prognostic label database 212, and/or ameliorative process label 144 database 216 as a result. As a further example, a medical and/or academic paper, or a study on which it was based, may be revoked; classification device 104 may remove it from first training set 124, second training set 136, physiological sample database 200, expert knowledge database 204, prognostic label database 212, and/or ameliorative process label 144 database 216 as a result. Information provided by an expert may likewise be removed if the expert loses credentials or is revealed to have acted fraudulently.

Continuing to refer to FIG. 2, elements of data of first training set 124, second training set 136, physiological sample database 200, expert knowledge database 204, prognostic label database 212, and/or ameliorative process label 144 database 216 may have temporal attributes, such as timestamps; classification device 104 may order such elements according to recency, select only elements more recently entered for first training set 124 and/or second training set 136, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Referring again to FIG. 1, machine-learning module 116 is configured to generate at least a diagnostic output using machine learning as a function of the at least an expert submission and the at least a physiological input. As used herein, a "diagnostic output" is an output containing at least a prognostic label and/or at least an ameliorative label, where the at least a prognostic label and/or at least an ameliorative label is output by machine-learning module 116 as a function of at least a physiological input. For example, and without limitation, a diagnostic output may include a prognostic label associated with at least a physiological input, such as a diagnosis of a condition, syndrome, or likely future condition or syndrome based on data collected as at least a biological sample or as a user query. As another non-limiting example, a diagnostic output may include an ameliorative process label 144 associated with a prognostic label and/or other datum of at least a physiological input; for instance, a diagnostic output may include a treatment for a symptom and/or condition described by a user and/or revealed in or as a result of a biological extraction. Persons skilled in the art, upon reviewing the entirety of this disclosure, will be aware of various additional examples for a diagnostic output as defined and described herein.

Still referring to FIG. 1, machine-learning module 116 may be designed and configured to generate at least a prognostic output by creating at least a machine-learning model relating data useable for at least a physiological input to data usable for at least a diagnostic output using training data 120 and generating the at least a diagnostic output using the at least a machine-learning model; at least a machine-learning model may include one or more models that determine a mathematical relationship between physiological state data and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Machine-learning may include other regression algorithms, including without limitation polynomial regression.

Continuing to refer to FIG. 1, machine-learning algorithm used to generate at least a machine-learning model may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, machine-learning module 116 may generate prognostic output using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 124; the trained network may then be used to apply detected relationships between physiological input data and diagnostic output data.

Continuing to refer to FIG. 1, machine-learning module 116 may generate at least a machine-learning model using one or more supervised machine learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological input data as inputs, elements of data usable for diagnostic outputs as outputs, and a scoring function representing a desired form of relationship to be detected between inputs and outputs; scoring function may, for instance, seek to maximize the probability that a input and/or combination of inputs is associated with a given outputs or combination of outputs, to minimize the probability that a given input and/or combination of inputs is not associated with a given output and/or combination of outputs. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 124. Persons skilled in the art, upon reviewing the entirety of this disclosure, will be aware of various possible variations of supervised machine learning algorithms that may be used to determine relation between inputs and outputs. In an embodiment, one or more supervised machine-learning algorithms may be restricted to a particular domain for instance, a supervised machine-learning process may be performed with respect to a given set of parameters and/or categories of parameters that have been suspected to be related to a given set of diagnostic output data, and/or are specified as linked to a medical specialty and/or field of medicine covering a particular set of diagnostic output data. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data 120. Domain restrictions may be suggested by experts and/or deduced from known purposes for particular evaluations and/or known tests used to evaluate input data. Additional supervised learning processes may be performed without domain restrictions to detect, for instance, previously unknown and/or unsuspected relationships between input data and output data.

Still referring to FIG. 1, machine-learning module 116 may generate at least a machine-learning model using one or more unsupervised processes. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, machine-learning module 116 and/or classification device 104 may perform an unsupervised machine learning process on training data 120, which may cluster data of training data 120 according to detected relationships between elements of training data 120, including without limitation correlations of elements of physiological state data to each other, correlations of prognostic labels to each other, and/or ameliorative process labels 144 to each other; such relations may then be combined with supervised machine learning results to add new criteria for machine-learning module 116 to apply in relating inputs to outputs.

Still referring to FIG. 1, classification device 104 and/or machine-learning module 116 may detect further significant categories of physiological input data and/or relationships of such categories to diagnostic output data, using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, machine-learning module 116 and/or classification device 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 1, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 1, machine-learning module 116 may alternatively or additionally be designed and configured to generate at least a diagnostic output by executing a lazy learning process as a function of the first training set 124 and the at least a biological extraction. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a diagnostic output associated with at least a physiological input, using training data 120. As a non-limiting example, an initial heuristic may include a ranking of diagnostic output data according to relation to a test type of at least a biological extraction, one or more categories of physiological data identified in test type of at least a biological extraction, one or more values detected in at least a biological extraction, and/or one or more prognostic or ameliorative process labels 144; ranking may include, without limitation, ranking according to significance scores of associations between elements of physiological input data and diagnostic output data, for instance as calculated as described above. Heuristic may include selecting some number of highest-ranking associations and/or diagnostic output data. Machine-learning module 116 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 1, machine-learning module 116 may generate a plurality of diagnostic outputs having different implications for a particular human subject. In such a situation, machine-learning module 116 and/or classification device 104 may perform additional processes to filter diagnostic outputs. Filtering diagnostic outputs may include filtering according to at least an expert submission; in an embodiment this may include presenting multiple possible results to a medical practitioner, informing the medical practitioner that one or more follow-up tests and/or physiological samples are needed to further determine a more definite prognostic label. Alternatively or additionally, expert submission may be received prior to generation of plurality of diagnostic outputs. Processes may alternatively or additionally include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, machine-learning module 116 and/or classification device 104 may operate a further algorithm to determine which of the multiple outputs is most likely to be correct; algorithm may include use of an additional supervised and/or unsupervised model. Alternatively or additionally, machine-learning module 116 may perform one or more lazy learning processes using a more comprehensive set of user data to identify a more probably correct result of the multiple results. Results may be presented and/or retained with rankings, for instance to advise a medical professional of the relative probabilities of various diagnostic outputs being correct; alternatively or additionally, diagnostic outputs associated with a probability of correctness below a given threshold and/or diagnostic outputs contradicting results of the additional process, may be eliminated. Persons skilled in the art, upon reviewing the entirety of this disclosure, will be aware of various ways in which additional processing may be used to determine relative likelihoods of diagnostic outputs on a list of multiple diagnostic outputs, and/or to eliminate some labels from such a list.

Still referring to FIG. 1, machine-learning module 116 is configured to generate at least a diagnostic output as a function of at least an expert submission. For instance, and without limitation, machine learning module may be configured to generate a plurality of diagnostic outputs and filter the plurality of diagnostic outputs using the at least a diagnostic constraint, for instance as described above. Machine-learning module 116 may alternatively or additionally be configured to filter training data 120 according to the at least a diagnostic constraint and/or expert submission. For instance, an expert may enter a submission limiting training data 120 to a cohort including human subject, which may be any cohort as described in this disclosure; submission may be entered, for instance, as an expert input indicating interest in all persons sharing one or more characteristics with human subject, such as all persons within a similar age range to human subject, within an ethnic group matching the human subject, having the same sex as the human subject, having similar symptoms, habits of eating, exercise or the like to the human subject, labeled with the same prognostic label or labels as human subject, or the like. Persons skilled in the art, upon reviewing the entirety of this disclosure will be aware of various examples of ways to filter training data 120 according to at least an expert submission and/or at least a diagnostic constraint and/or expert submission. Machine-learning module 116 may be configured to generate the plurality of diagnostic outputs according to the at least an expert submission by generating a plurality of diagnostic outputs and rank the plurality of diagnostic outputs using the at least an expert submission and/or diagnostic constraint.

In an embodiment, and continuing to refer to FIG. 1, where machine-learning module 116 generates a plurality of machine-learning models, machine-learning module 116 may be configured to generate the at least a diagnostic output as a function of the at least an expert submission by selecting a machine-learning model as a function of the at least a diagnostic constraint and/or the at least an expert submission and generating the at least a diagnostic output using the selected machine-learning model. Selecting a machine-learning model as a function of the at least diagnostic constraint may include selecting a machine-learning model that was generated according to a constraint matching the at least a diagnostic constraint. For instance, training data 120 may have been organized according to one or more diagnostic constraints, and machine-learning module 116 may have previously generated a plurality of machine-learning models using a plurality of filtered training datasets. As a non-limiting example, a machine-learning model may be generated for each of a list of common conditions, for each of a list of common tests used to record biometric samples, or any other category of medical data of interest to experts and/or doctors; expert submissions collected as described above may list categories and/or cohorts of data for which machine-learning modules 116 are desirable, and machine-learning module 116 may generate models from training data 120 organized according to such categories and/or cohorts. List of categories and/or cohorts may be provided via a graphical user interface 108 to an expert providing the at least an expert submission; expert may enter at least an expert submission by selecting one such category and/or cohort. Machine-learning module 116 may be configured to generate the at least a diagnostic output as a function of the at least an expert submission by combining at least a diagnostic output with the at least an expert submission; expert submission may be appended to, concatenated with, included with, and/or otherwise combined with at least a diagnostic output.

With continued reference to FIG. 1, machine-learning module 116 may include a prognostic label learner 148 operating on the classification device 104, the prognostic label learner 148 designed and configured to generate the at least a prognostic output as a function of the first training set 124 and the at least a biological extraction. Prognostic label learner 148 may include any hardware and/or software module. Prognostic label learner 148 may be designed and configured to generate outputs using machine learning processes as described above.

Still referring to FIG. 1, prognostic label learner 148 may be designed and configured to generate at least a prognostic output by creating at least a first machine-learning model 152 relating physiological state data to prognostic labels using the first training set 124 and generating the at least a prognostic output using the first machine-learning model 152; at least a first machine-learning model 152 may include one or more models that determine a mathematical relationship between physiological state data and prognostic labels, and/or neural-net models, as described above.

Still referring to FIG. 1, prognostic label learner 148 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 124; the trained network may then be used to apply detected relationships between elements of physiological state data and prognostic labels.

Figure 7:
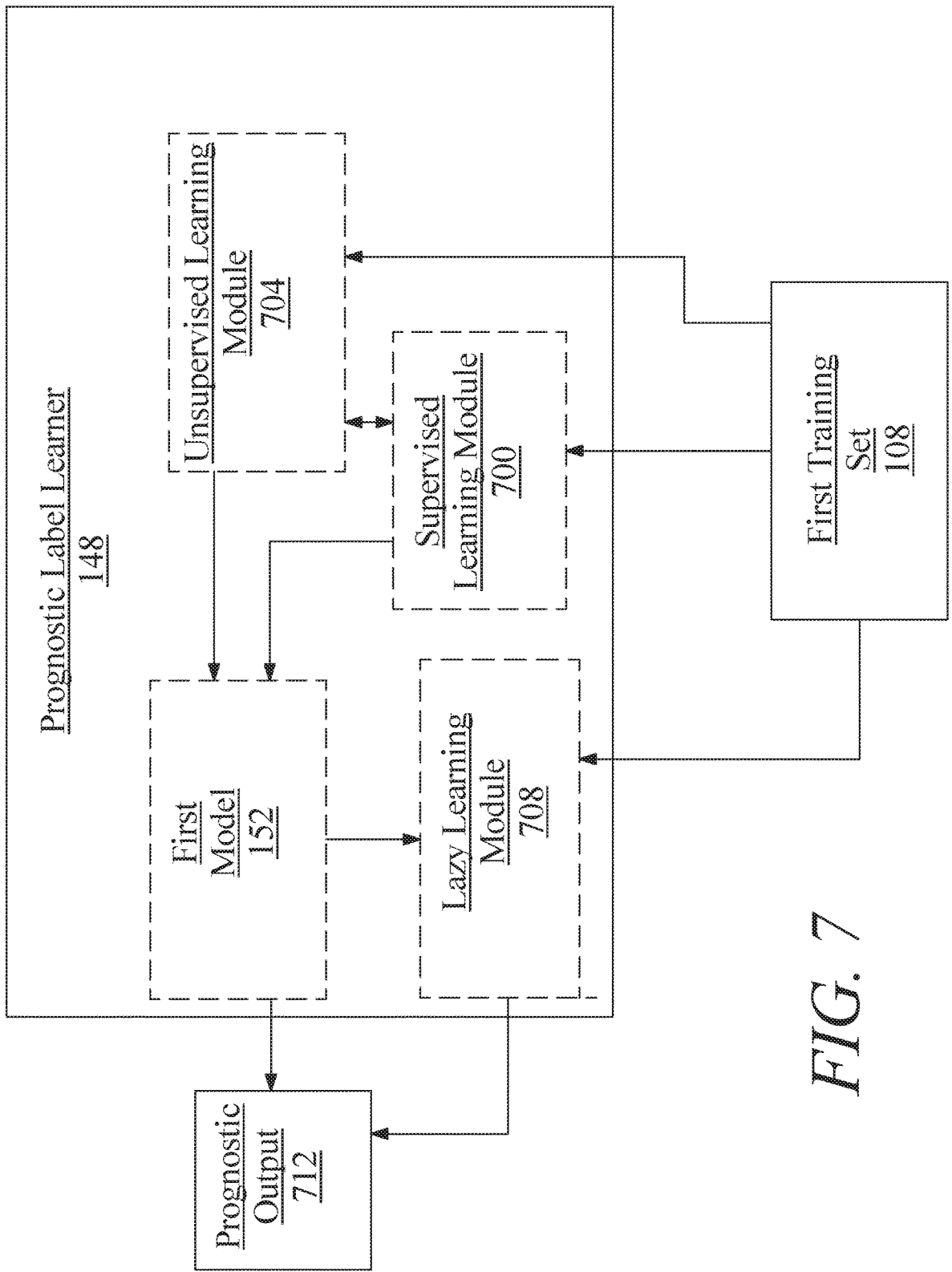
FIG. 7 is a block diagram illustrating an exemplary embodiment of a prognostic label learner 148 and associated system elements.

Referring now to FIG. 7, machine-learning algorithms used by prognostic label learner 148 may include supervised machine-learning algorithms, which may, as a non-limiting example be executed using a supervised learning module 700 executing on classification device 104 and/or on another computing device in communication with classification device 104, which may include any hardware or software module. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data 128 and/or combination of elements of physiological data is associated with a given prognostic label and/or combination of prognostic labels to minimize the probability that a given element of physiological state data 128 and/or combination of elements of physiological state data is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 124. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data 120. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Still referring to FIG. 7, machine-learning algorithms may include unsupervised processes; unsupervised processes may, as a non-limiting example, be executed by an unsupervised learning module 704 executing on classification device 104 and/or on another computing device in communication with classification device 104, which may include any hardware or software module. For instance, and without limitation, prognostic label learner 148 and/or classification device 104 may perform an unsupervised machine learning process on first training set 124, which may cluster data of first training set 124 according to detected relationships between elements of the first training set 124, including without limitation correlations of elements of physiological state data to each other and correlations of prognostic labels to each other; such relations may then be combined with supervised machine learning results to add new criteria for prognostic label learner 148 to apply in relating physiological state data to prognostic labels. As a non-limiting, illustrative example, an unsupervised process may determine that a first element of physiological data acquired in a blood test correlates closely with a second element of physiological data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data 128 and second element of physiological state data 128 may indicate that the second element is also a good predictor for the prognostic label; second element may be included in a new supervised process to derive a relationship or may be used as a synonym or proxy for the first physiological element by prognostic label learner 148.

With continued reference to FIG. 7, classification device 104 and/or prognostic label learner 148 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, prognostic label learner 148 and/or classification device 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 7, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 7, prognostic label learner 148 may alternatively or additionally be designed and configured to generate at least a prognostic output by executing a lazy learning process as a function of the first training set 124 and the at least a biological extraction; lazy learning processes may be performed by a lazy learning module 708 executing on classification device 104 and/or on another computing device in communication with classification device 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 124. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 148 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 7, prognostic label learner 148 may generate a plurality of prognostic labels having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 148 and/or classification device 104 may perform additional processes to resolve ambiguity. Processes may include filtering, sorting, and/or ranking plurality of prognostic labels according to at least an expert submission and/or diagnostic constraint as described above. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, prognostic label learner 148 and/or classification device 104 may operate a further algorithm to determine which of the multiple outputs is most likely to be correct; algorithm may include use of an additional supervised and/or unsupervised model. Alternatively or additionally, prognostic label learner 148 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 712 may be provided to client device as described in further detail below.

Referring again to FIG. 1, machine-learning module 116 may include an ameliorative process label learner 156 operating on the classification device 104, the ameliorative process label learner 156 designed and configured to generate the at least an ameliorative output as a function of the second training set 136 and the at least a prognostic output. Ameliorative process label learner 156 may include any hardware or software module suitable for use as a prognostic label learner 148 as described above. Ameliorative process label learner 156 is a machine-learning module 116 as described above; ameliorative process label learner 156 may perform any machine-learning process or combination of processes suitable for use by a prognostic label learner 148 as described above. For instance, and without limitation, and ameliorative process label learner 156 may be configured to create a second machine-learning model 160 relating prognostic labels to ameliorative labels using the second training set 136 and generate the at least an ameliorative output using the second machine-learning model 160; second machine-learning model 160 may be generated according to any process, process steps, or combination of processes and/or process steps suitable for creation of first machine learning model. In an embodiment, ameliorative process label learner 156 may use data from first training set 124 as well as data from second training set 136; for instance, ameliorative process label learner 156 may use lazy learning and/or model generation to determine relationships between elements of physiological data, in combination with or instead of prognostic labels, and ameliorative labels. Where ameliorative process label learner 156 determines relationships between elements of physiological data and ameliorative labels directly, this may determine relationships between prognostic labels and ameliorative labels as well owing to the existence of relationships determined by prognostic label learner 148.

Figure 8:
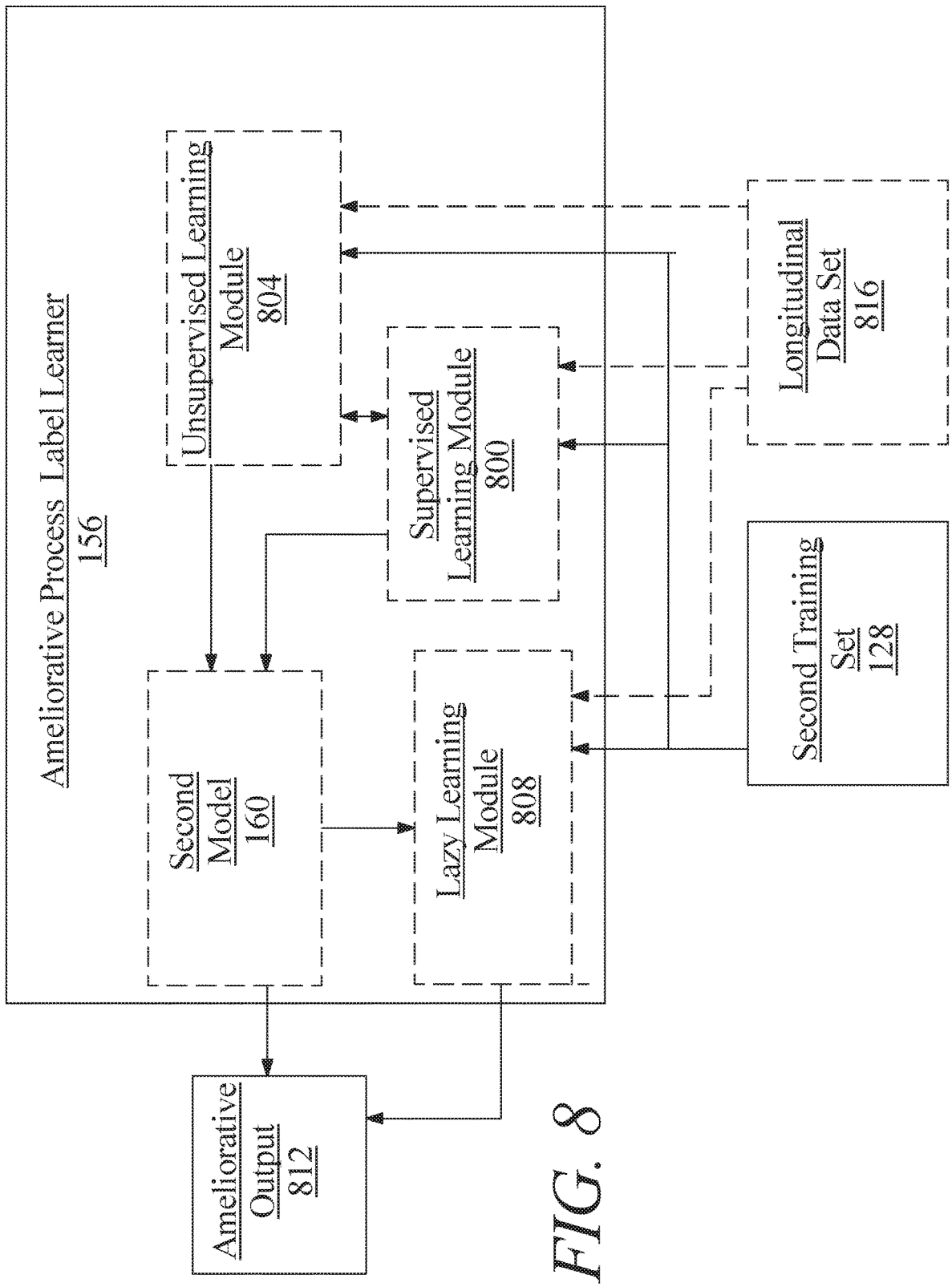
FIG. 8 is a block diagram illustrating an exemplary embodiment of an ameliorative process label learner 156 and associated system elements.

Referring now to FIG. 8, ameliorative process label learner 156 may be configured to perform one or more supervised learning processes, as described above; supervised learning processes may be performed by a supervised learning module 800 executing on classification device 104 and/or on another computing device in communication with classification device 104, which may include any hardware or software module. For instance, a supervised learning algorithm may use prognostic labels as inputs, ameliorative labels as outputs, and a scoring function representing a desired form of relationship to be detected between prognostic labels and ameliorative labels; scoring function may, for instance, seek to maximize the probability that a given prognostic label and/or combination of prognostic labels is associated with a given ameliorative label and/or combination of ameliorative labels to minimize the probability that a given prognostic label and/or combination of prognostic labels is not associated with a given ameliorative label and/or combination of ameliorative labels. In an embodiment, one or more supervised machine-learning algorithms may be restricted to a particular domain; for instance, a supervised machine-learning process may be performed with respect to a given set of parameters and/or categories of prognostic labels that have been suspected to be related to a given set of ameliorative labels, for instance because the ameliorative processes corresponding to the set of ameliorative labels are hypothesized or suspected to have an ameliorative effect on conditions represented by the prognostic labels, and/or are specified as linked to a medical specialty and/or field of medicine covering a particular set of prognostic labels and/or ameliorative labels. As a non-limiting example, a particular set prognostic labels corresponding to a set of cardiovascular conditions may be typically treated by cardiologists, and a supervised machine-learning process may be performed to relate those prognostic labels to ameliorative labels associated with various treatment options, medications, and/or lifestyle changes.

With continued reference to FIG. 8, ameliorative process label learner 156 may perform one or more unsupervised machine-learning processes as described above; unsupervised processes may be performed by an unsupervised learning module 804 executing on classification device 104 and/or on another computing device in communication with classification device 104, which may include any hardware or software module. For instance, and without limitation, ameliorative process label learner 156 and/or classification device 104 may perform an unsupervised machine learning process on second training set 136, which may cluster data of second training set 136 according to detected relationships between elements of the second training set 136, including without limitation correlations of prognostic labels to each other and correlations of ameliorative labels to each other; such relations may then be combined with supervised machine learning results to add new criteria for ameliorative process label learner 156 to apply in relating prognostic labels to ameliorative labels. As a non-limiting, illustrative example, an unsupervised process may determine that a first prognostic label 132 correlates closely with a second prognostic label 140, where the first prognostic label 132 has been linked via supervised learning processes to a given ameliorative label, but the second has not; for instance, the second prognostic label 140 may not have been defined as an input for the supervised learning process, or may pertain to a domain outside of a domain limitation for the supervised learning process. Continuing the example, a close correlation between first prognostic label 132 and second prognostic label 140 may indicate that the second prognostic label 140 is also a good match for the ameliorative label; second prognostic label 140 may be included in a new supervised process to derive a relationship or may be used as a synonym or proxy for the first prognostic label 132 by ameliorative process label learner 156. Unsupervised processes performed by ameliorative process label learner 156 may be subjected to any domain limitations suitable for unsupervised processes performed by prognostic label learner 148 as described above.

Still referring to FIG. 8, classification device 104 and/or ameliorative process label learner 156 may detect further significant categories of prognostic labels, relationships of such categories to ameliorative labels, and/or categories of ameliorative labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, ameliorative process label learner 156 and/or classification device 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

Continuing to view FIG. 8, ameliorative process label learner 156 may be configured to perform a lazy learning process as a function of the second training set 136 and the at least a prognostic output to produce the at least an ameliorative output; a lazy learning process may include any lazy learning process as described above regarding prognostic label learner 148. Lazy learning processes may be performed by a lazy learning module 808 executing on classification device 104 and/or on another computing device in communication with classification device 104, which may include any hardware or software module. Ameliorative output 812 may be provided to a client device 164 as described in further detail below.

In an embodiment, and still referring to FIG. 8, ameliorative process label learner 156 may generate a plurality of ameliorative process labels 144 having different implications for a particular person. For instance, where a prognostic label indicates that a person has a magnesium deficiency, various dietary choices may be generated as ameliorative labels associated with correcting the deficiency, such as ameliorative labels associated with consumption of almonds, spinach, and/or dark chocolate, as well as ameliorative labels associated with consumption of magnesium supplements. In such a situation, ameliorative process label learner 156 and/or classification device 104 may perform additional processes to resolve ambiguity. Processes may include presenting multiple possible results to a medical practitioner, informing the medical practitioner of various options that may be available, and/or that follow-up tests, procedures, or counseling may be required to select an appropriate choice. Alternatively or additionally, processes may include additional machine learning steps. For instance, ameliorative process label learner 156 may perform one or more lazy learning processes using a more comprehensive set of user data to identify a more probably correct result of the multiple results. Results may be presented and/or retained with rankings, for instance to advise a medical professional of the relative probabilities of various ameliorative labels being correct or ideal choices for a given person; alternatively or additionally, ameliorative labels associated with a probability of success or suitability below a given threshold and/or ameliorative labels contradicting results of the additional process, may be eliminated. As a non-limiting example, an additional process may reveal that a person is allergic to tree nuts, and consumption of almonds may be eliminated as an ameliorative label to be presented.

Continuing to refer to FIG. 8, ameliorative process label learner 156 may be designed and configured to generate further training data 120 and/or to generate outputs using longitudinal data 816. As used herein, longitudinal data 816 may include a temporally ordered series of data concerning the same person, or the same cohort of persons; for instance, longitudinal data 816 may describe a series of blood samples taken one day or one month apart over the course of a year. Longitudinal data 816 may related to a series of samples tracking response of one or more elements of physiological data recorded regarding a person undergoing one or more ameliorative processes linked to one or more ameliorative process labels 144. Ameliorative process label learner 156 may track one or more elements of physiological data and fit, for instance, a linear, polynomial, and/or splined function to data points; linear, polynomial, or other regression across larger sets of longitudinal data, using, for instance, any regression process as described above, may be used to determine a best-fit graph or function for the effect of a given ameliorative process over time on a physiological parameter. Functions may be compared to each other to rank ameliorative processes; for instance, an ameliorative process associated with a steeper slope in curve representing improvement in a physiological data element, and/or a shallower slope in a curve representing a slower decline, may be ranked higher than an ameliorative process associated with a less steep slope for an improvement curve or a steeper slope for a curve marking a decline. Ameliorative processes associated with a curve and/or terminal data point representing a value that does not associate with a previously detected prognostic label may be ranked higher than one that is not so associated. Information obtained by analysis of longitudinal data 816 may be added to ameliorative process database and/or second training set 136.

Referring again to FIG. 1, classification device 104 may be configured to transmit an output including at least a diagnostic output to a client device 164. A client device 164 may include, without limitation, a display in communication with classification device 104; display may include any display as described below in reference to FIG. 10. A client device 164 may include an addition computing device, such as a mobile device, laptop, desktop computer, or the like; as a non-limiting example, the client device 164 may be a computer and/or workstation operated by a medical professional. Output may be displayed on at least a client device 164 using an output graphical user interface 108; output graphical user interface 108 may display one or more prognostic labels of prognostic output and/or one or more ameliorative labels of ameliorative output. Alternatively or additionally, prognostic labels and/or ameliorative labels may be translated into display data including without limitation textual descriptions corresponding to prognostic labels and/or ameliorative labels, one or more images associated with prognostic labels and/or ameliorative labels, and/or one or more video or audio files associated with prognostic labels and/or ameliorative labels; each of the above-described display data may be retrieved from a display data store, which may, for instance associate or link prognostic labels, ameliorative labels, and/or elements of physiological data with one or more display data. Where output includes multiple prognostic labels and/or multiple ameliorative labels, classification device 104 may cause to a client device 164 to display the multiple labels and/or display data associated therewith; labels may be displayed according to rankings as described above, including without limitation rankings of prognostic labels according to probability of correctness, ranking of ameliorative labels according to probability of efficacy, or the like. Significance scores, as calculated above, may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated.

With continued reference to FIG. 1, classification device 104 may be configured to display one or more follow-up suggestions at a client device 164. One of more follow-up suggestions may include, without limitation, suggestions for acquisition of an additional biological extraction, physiological input, and/or expert submission; in an embodiment, additional biological extraction may be provided to classification device 104, which may trigger repetition of one or more processes as described above, including without limitation generation of prognostic output, refinement or elimination of ambiguous prognostic labels of prognostic output, generation of ameliorative output, and/or refinement or elimination of ambiguous ameliorative labels of ameliorative output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any physiological sample as described above.

With continued reference to FIG. 1, classification device 104 may display one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with system 100. Contextual information may include one or more questions a patient wishes to have answered in a medical visit and/or session, and/or as a result of interaction with system 100. Contextual information may include one or more questions to ask a patient. Persons skilled in the art, upon reviewing the entirety of this disclosure, will be aware of various forms of contextual information that may be included, consistently with this disclosure. System 100 may record a conversation between a patient and a medical professional for later entry into medical records. Transmitting and/or generation of at least a diagnostic output may include transmitting a machine learning model to client device; machine learning model may configure the client device to output the at least a diagnostic output.

Embodiments of system 100 may furnish augmented intelligence systems that facilitate diagnostic, prognostic, curative, and/or therapeutic decisions by medical professionals such as doctors. System 100 may provide fully automated tools and resources for each doctor to handle, process, diagnosis, develop treatment plans, facilitate and monitor all patient implementation, and record each patient status. Provision of expert system elements via expert inputs and document-driven language analysis may ensure that recommendations generated by system 100 are backed by the very best medical knowledge and practices in the world. Models and/or learners with access to data in depth may enable generation of recommendations that are directly personalized for each patient, providing complete confidence, mitigated risk, and complete transparency. Access to well-organized and personalized knowledge in depth may greatly enhance efficiency of medical visits; in embodiments, a comprehensive visit may be completed in as little as 10 minutes. Recommendations may further suggest follow up testing and/or therapy, ensuring an effective ongoing treatment and prognostic plan.

Figure 9:
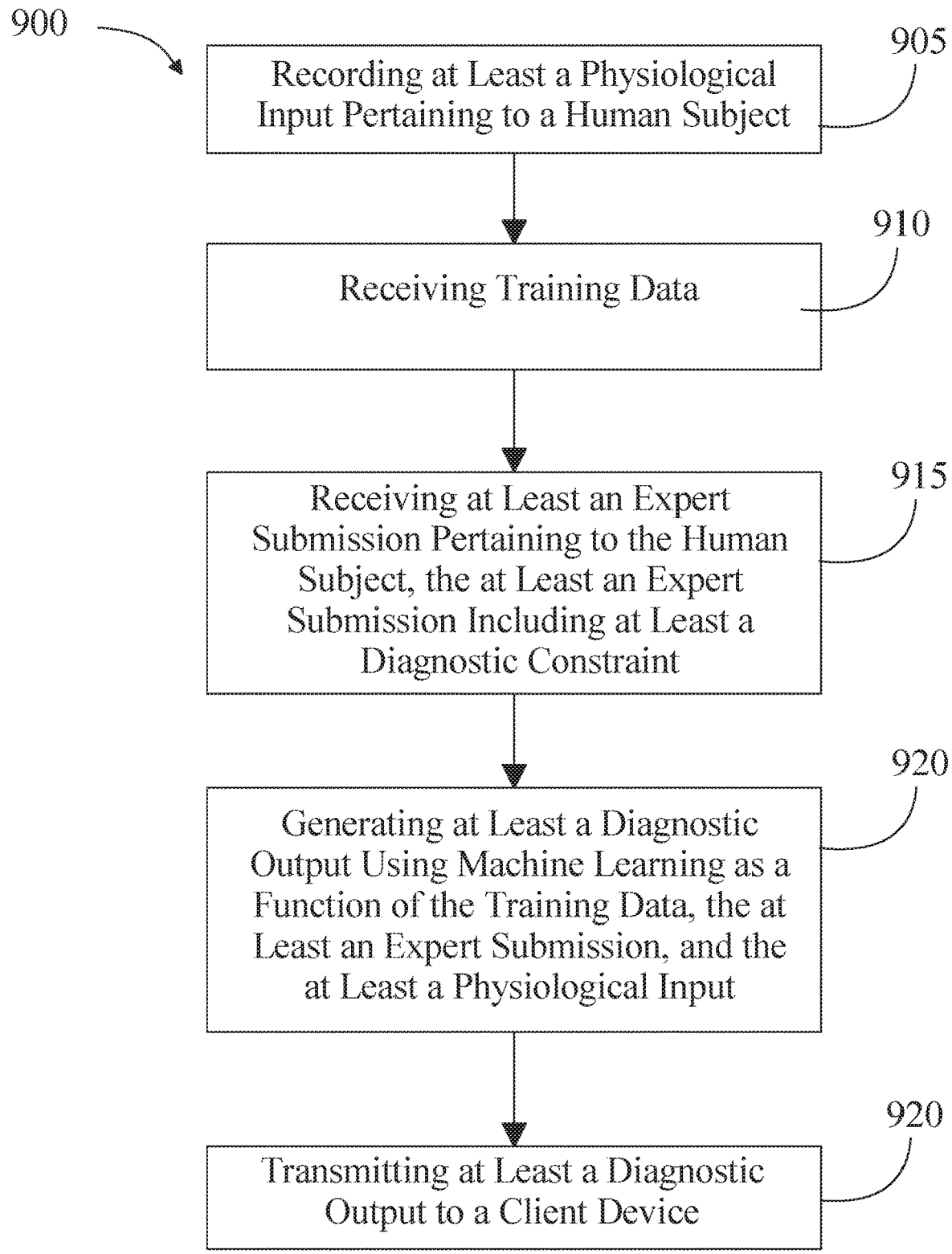
FIG. 9 illustrates flow diagram illustrating an exemplary embodiment of a method of classification to prognostic labels.

Referring now to FIG. 9, an exemplary embodiment of a method 900 of classification to prognostic labels using expert submissions is illustrated. At step 905, a classification device 104 records at least a physiological input pertaining to a human subject; this may be performed as described above in reference to FIGS. 1-8. For instance, a person who is suffering from a physical complaint, such as knee pain, may enter a textual submission via a graphical user interface 108, by means of electronic communication, or the like describing the physical complaint; the person may alternatively or additionally describe the physical complaint through any suitable means or method of communication to a medical professional or other expert, who may enter the description according to any process described above. A persons who is suffering from a psychological, emotional, or other constitutionally relevant complaint may similarly submit, enter, or provide information concerning the complaint to a medical professional graphical user interface 108. A person may similarly enter questions regarding physical, emotional, psychological, nutritional, pharmaceutical, or other matters, questions about current and/or past treatment of the person or persons having similar conditions, demographic factors, or the like, and/or a description of current and/or past treatment, questions, and/or complaints. Each such entry provided from a person may be entered by any means or methods described above for entry of at least an expert submission, including entry using a graphical user interface 108, entry of a textual submission that is analyzed by a language processing module 112, or the like. At least a physiological input may include any biological extraction as described above; biological extraction may be retrieved from medical records, entered by an expert such as a medical professional, entered and/or provided by human subject, and/or received from at least a sensor including without limitation a wearable device. As a non-limiting example, a person may approach an expert such as a doctor with a question or complaint, and the expert may order recording of a biological extraction by having a test performed on user, retrieving medical records regarding the user, having the user fill out a questionnaire, or the like; this may be performed iteratively as described in further detail below.

At step 910, and with continued reference to FIG. 9, classification device 104 receives at least an expert submission pertaining to the human subject, the at least an expert submission including at least a diagnostic constraint; this may be performed as described above in reference to FIGS. 1-8. As a non-limiting example, where human subject is a person who is visiting a doctor's office or otherwise consulting with an expert, expert may eliminate certain categories and/or descriptions of data describable by physiological state data, prognostic labels, ameliorative process labels 144, or the like, may select particular topics of interest, getting more focused training data 120 and/or models, may enter one or more demographic, age, or other facts re user, past diagnoses, past treatment, or may otherwise limit or focus questions to be answered or ranges of answers desired. In an embodiment, at least an expert submission includes a textual submission and receiving the expert submission includes parsing the at least a textual submission and extract the at least a diagnostic constraint using a language processing module 112, for instance as described above in reference to FIGS. 1-8.

At step 915, and still referring to FIG. 9, classification device 104 receives training data 120 relating physiological input data to diagnostic data; this may be implemented as described above in reference to FIGS. 1-8. At step 920, classification device 104 generates at least a diagnostic output using machine learning as a function of the at least an expert submission and the at least a physiological input. This may be performed as described above in reference to FIGS. 1-8. For instance, and without limitation, generating the at least a diagnostic output as a function of the at least an expert submission may include filtering the training data 120 according to the at least a diagnostic constraint. As a further non-limiting example, generating the at least a diagnostic output as a function of the at least an expert submission may include generating a plurality of machine-learning models, selecting a machine-learning model as a function of the at least a diagnostic constraint, and generating the at least a diagnostic output using the selected machine-learning model, for instance as described above in reference to FIGS. 1-8. As a further example, generating the at least a diagnostic output as a function of the at least an expert submission may include generating a plurality of diagnostic outputs and filtering the plurality of diagnostic outputs using the at least a diagnostic constraint. As another non-limiting example, generating the at least a diagnostic output as a function of the at least an expert submission may include generating a plurality of diagnostic outputs and ranking the plurality of diagnostic outputs using the at least an expert submission; this may be implemented as described above in reference to FIGS. 1-8. Generating the at least a diagnostic output as a function of the at least an expert may include combining a machine-learning output with the at least an expert submission, for instance as described above in reference to FIGS. 1-8.

Still referring to FIG. 9, training data 120 may include a first training set 124 including a plurality of first data entries, each first data entry of the first training set 124 including at least an element of physiological state data 128 and at least a correlated first prognostic label 132, for instance as described above in reference to FIGS. 1-8. Generating at least a diagnostic output as a function of the at least an expert submission generating at least a prognostic output as a function of the first training set 124 and the at least a physiological test sample. Training data 120 may include a second training set 136 including a plurality of second data entries, each second data entry of the first training set 124 including at least a second prognostic label 140 and at least a correlated ameliorative process label 144, for instance as described above in reference to FIGS. 1-8. Generating at least a diagnostic output as a function of the at least an expert submission may include generating the at least an ameliorative output as a function of the second training set 136 and at least a prognostic label.

At step 925, classification device 104 transmits at least a diagnostic output to a client device 164; this may be implemented as described above in reference to FIGS. 1-8. For instance, an expert such as a doctor may receive output generated by above-described steps and/or system components, and may initiate one or more processes as described above a second or third time; new changed and/or updated physiological input and/or expert submission may be provided, such as additional information eliminating possible prognostic labels and/or ameliorative labels, additional biological extraction data and/or data provided by user, additional diagnostic constraints, or the like. A doctor may, for instance, view an output suggesting two or more likely disease conditions and/or treatments, and eliminate one or the other based on professional judgement, personal and/or expert knowledge, and/or information provided by human subject concerning the latter's condition, history, and/or preferences. Similarly, a doctor or other expert may order follow-up tests based on personal and/or professional knowledge to obtain further constitutional and/or ameliorative information concerning human subject. As previously noted, any embodiment of method 900, of any other method explicitly or implicitly disclosed in this disclosure, or any step or combination of steps thereof, may be performed iteratively.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
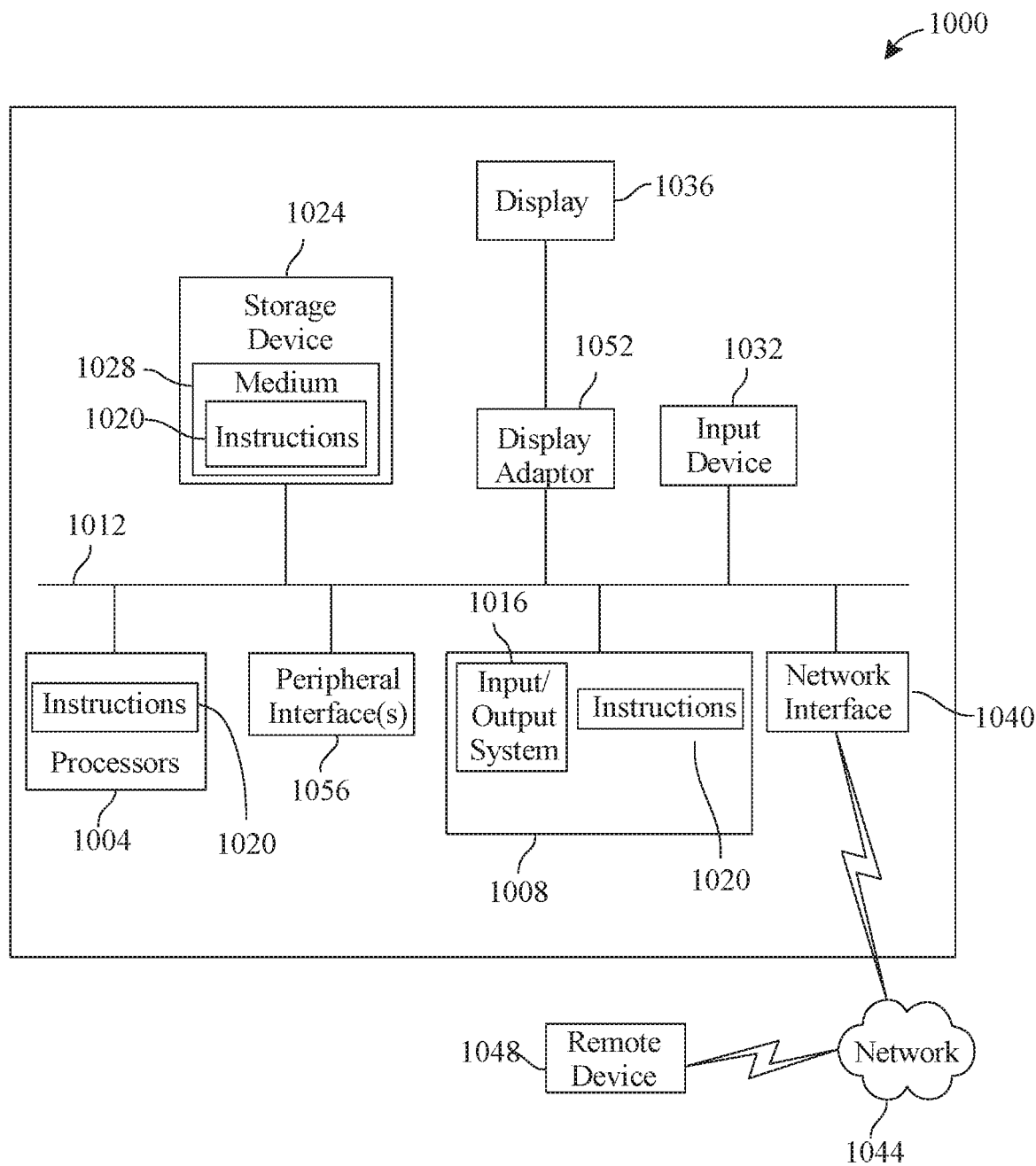
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 10310, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for classification to prognostic labels using expert inputs, the system comprising:
 a classification device, the classification device designed and configured to:
  record at least a physiological input pertaining to a human subject;
  receive at least an expert submission pertaining to the human subject, the at least an expert submission including at least a diagnostic constraint identifying a cohort related to the at least a physiological input; and
  transmit at least a diagnostic output to a client device;
 wherein the at least an expert submission further comprises a textual submission; and
 the classification device further comprises a language processing module designed and configured to parse the at least a textual submission and extract the at least a diagnostic constraint, wherein each word in the textual submission is represented by a vector, and wherein cosine similarity is used to determine the degree of similarity between the vectors representing each word; and
 a machine-learning module operating on the classification device, the machine-learning module designed and configured to:
  receive training data relating physiological input data to diagnostic data;
  filter the training data according to the cohort related to the at least a physiological input;
  generate at least a diagnostic output using a trained neural network as a function of the filtered training data, the at least an expert submission and the at least a physiological input, said diagnostic output identifying a treatment for the human subject; and
  generate a subset of the diagnostic output as a function of the diagnostic constraint.

2. The system of claim 1, wherein:
 the machine learning module is configured to generate a plurality of machine-learning models; and
 the machine-learning module is configured to generate the at least a diagnostic output by:
  selecting a machine-learning model as a function of the cohort related to the at least a physiological input; and
  generating the at least a diagnostic output, identifying a treatment for the human subject, using the selected machine-learning model.

3. The system of claim 1, wherein the machine learning module is configured to generate the at least a diagnostic output by:
 generating a plurality of diagnostic outputs; and
 filtering the plurality of diagnostic outputs using the cohort related to the at least a physiological input.

4. The system of claim 1, wherein the machine-learning module is further configured to generate a plurality of diagnostic outputs and rank the plurality of diagnostic outputs using the at least an expert submission.

5. The system of claim 1, wherein the machine-learning module is further configured to combine a machine-learning output with the at least an expert submission.

6. The system of claim 1, wherein:
 the training data further comprises a first training set including a plurality of first data entries, each first data entry of the first training set including at least an element of physiological state data and at least a correlated first prognostic label; and
 the machine-learning module further comprises a prognostic label learner operating on the classification device, the prognostic label learner designed and configured to generate at least a prognostic output as a function of the first training set and the at least a physiological test sample.

7. The system of claim 1, wherein:
 the training data further comprises a second training set including a plurality of second data entries, each second data entry of the first training set including at least a second prognostic label and at least a correlated ameliorative process label; and
 the machine-learning module an ameliorative label learner operating on the classification device, the ameliorative label learner designed and configured to generate at least an ameliorative output as a function of the second training set and at least a prognostic label.

8. A method of classification to prognostic labels using expert inputs, the method comprising:

recording, at a classification device, at least a physiological input, including data derived from at least one biological extraction, pertaining to a human subject;

receiving, at the classification device, at least an expert submission pertaining to the human subject, the at least an expert submission including at least a diagnostic constraint identifying a cohort related to the at least a physiological input;

wherein the at least an expert submission further comprises a textual submission; and the classification device further comprises a language processing module designed and configured to parse the at least a textual submission and extract the at least a diagnostic constraint, wherein each word in the textual submission is represented by a vector, and wherein cosine similarity is used to determine the degree of similarity between the vectors representing each word;

receiving, at the classification device, training data relating physiological input data to diagnostic data;

filtering the training data according to the cohort related to the at least a physiological input;

generating, by the classification device, at least a diagnostic output using a trained neural network as a function of the filtered training data, the at least an expert submission and the at least a physiological input, said diagnostic output identifying a treatment for the human subject;

generating a subset of the at least a diagnostic output as a function of a diagnostic constraint; and transmitting, by the classification device, the subset of the at least a diagnostic output to a client device.

9. The method of claim 8, wherein generating the at least a diagnostic output as a function of the at least an expert submission further comprises:

generating a plurality of machine-learning models;

selecting a machine-learning model as a function of the cohort related to the at least a physiological input; and generating the at least a diagnostic output, identifying a treatment for the human subject, using the selected machine-learning model.

10. The method of claim 8, wherein generating the at least a diagnostic output as a function of the at least an expert submission further comprises:

generating a plurality of diagnostic outputs; and filtering the plurality of diagnostic outputs using the cohort related to the at least a physiological input.

11. The method of claim 8, wherein generating the at least a diagnostic output as a function of the at least an expert submission further comprises generating a plurality of diagnostic outputs and ranking the plurality of diagnostic outputs using the at least an expert submission.

12. The method of claim 8, wherein generating the at least a diagnostic output as a function of the at least an expert submission further comprises combining a machine-learning output with the at least an expert submission.

13. The method of claim 8, wherein:

the training data further comprises a first training set including a plurality of first data entries, each first data entry of the first training set including at least an element of physiological state data and at least a correlated first prognostic label; and generating the at least a diagnostic output as a function of the at least an expert submission generating at least a prognostic output as a function of the first training set and the at least a physiological test sample.

14. The method of claim 8, wherein:

the training data further comprises a second training set including a plurality of second data entries, each second data entry of the first training set including at least a second prognostic label and at least a correlated ameliorative process label; and generating the at least a diagnostic output as a function of the at least an expert submission further comprises generating the at least an ameliorative output as a function of the second training set and at least a prognostic label.

\* \* \* \* \*